US010709852B2

(12) United States Patent
Engelbreth et al.

(10) Patent No.: US 10,709,852 B2
(45) Date of Patent: Jul. 14, 2020

(54) DELIVERY DEVICE AND KIT, AND METHOD OF USE

(71) Applicant: TRUDELL MEDICAL INTERNATIONAL, London (CA)

(72) Inventors: Daniel Engelbreth, London (CA); Martin P. Foley, London (CA); Jerry Grychowski, Batavia, IL (US); James Schmidt, London (CA); Jennifer Pevler, London (CA)

(73) Assignee: Trudell Medical International, London (CA)

( * ) Notice: Subject to any disclaimer, the term of this patent is extended or adjusted under 35 U.S.C. 154(b) by 1256 days.

(21) Appl. No.: 14/854,678

(22) Filed: Sep. 15, 2015

(65) Prior Publication Data

US 2016/0030687 A1 Feb. 4, 2016

Related U.S. Application Data

(63) Continuation of application No. PCT/IB2014/000360, filed on Mar. 14, 2014.
(Continued)

(51) Int. Cl.
*A61M 15/00* (2006.01)
*A61M 16/08* (2006.01)
(Continued)

(52) U.S. Cl.
CPC .......... *A61M 15/009* (2013.01); *A61M 11/02* (2013.01); *A61M 11/06* (2013.01);
(Continued)

(58) Field of Classification Search
CPC .......... A61M 15/0013; A61M 15/0016; A61M 15/0018; A61M 15/0021; A61M 16/0003;
(Continued)

(56) References Cited

U.S. PATENT DOCUMENTS 3,861,210 A 1/1975 Griverus
4,253,468 A * 3/1981 Lehmbeck .............. A61B 5/09 128/200.18

(Continued)

FOREIGN PATENT DOCUMENTS

WO WO 2011125061 A2 10/2011
WO WO 2011137905 A1 11/2011
WO WO 2012173992 A1 12/2012

OTHER PUBLICATIONS

Display poster board, Newhouse et al., Prototype InspiraChamber™ and SmootherMask® —A Unique System with Optimized Particle Size Selectivity and Minimal Dead Space, 5 pages (various enlarged views), shown at the American Thoracic Society Meeting, San Francisco, May 18-23, 2012.

*Primary Examiner* — Steven O Douglas
(74) *Attorney, Agent, or Firm* — Brinks Gilson & Lione

(57) ABSTRACT

A delivery device includes a toroidal shaped housing defining an interior chamber and a central open space. The housing includes an input port communicating with the interior chamber and a delivery port positioned on an inner periphery of the housing. The delivery port is in fluid communication between the interior chamber and the central open space. The delivery port is spaced from the input port, which is adapted to receive an aerosolized medicament. In another aspect, a kit includes an outer ring-like housing component and a plurality of differently configured inner ring-like housing components mateable with the outer ring-like housing to form a holding chamber. A method of delivering an inhalable substance is also provided. A mask, including mounting and sealing portions is also provided, together with a method of manufacturing such a mask. Delivery devices include various alternative adapters to be used with a mask and a substance dispenser.

28 Claims, 23 Drawing Sheets

Related U.S. Application Data

(60) Provisional application No. 61/792,583, filed on Mar. 15, 2013, provisional application No. 61/878,384, filed on Sep. 16, 2013, provisional application No. 61/904,765, filed on Nov. 15, 2013.

(51) Int. Cl.
| | |
|---|---|
| *A61M 11/06* | (2006.01) |
| *A61M 16/06* | (2006.01) |
| *A61M 16/20* | (2006.01) |
| *A61M 16/00* | (2006.01) |
| *A61M 11/02* | (2006.01) |
| *A61M 15/08* | (2006.01) |
| *A61M 16/14* | (2006.01) |
| *A61J 9/00* | (2006.01) |
| *A61M 11/00* | (2006.01) |
| *A61J 17/00* | (2006.01) |

(52) U.S. Cl.
CPC .... *A61M 15/0013* (2014.02); *A61M 15/0016* (2014.02); *A61M 15/0018* (2014.02); *A61M 15/0021* (2014.02); *A61M 15/0086* (2013.01); *A61M 15/08* (2013.01); *A61M 16/0003* (2014.02); *A61M 16/06* (2013.01); *A61M 16/0666* (2013.01); *A61M 16/0816* (2013.01); *A61M 16/14* (2013.01); *A61M 16/209* (2014.02); *A61J 9/00* (2013.01); *A61J 17/001* (2015.05); *A61M 11/002* (2014.02); *A61M 16/0833* (2014.02); *A61M 16/208* (2013.01); *A61M 2205/0233* (2013.01); *A61M 2205/0238* (2013.01); *A61M 2205/583* (2013.01); *A61M 2207/00* (2013.01); *A61M 2207/10* (2013.01); *A61M 2209/06* (2013.01); *A61M 2210/0618* (2013.01); *A61M 2210/1007* (2013.01); *A61M 2240/00* (2013.01)

(58) Field of Classification Search
CPC .... A61M 16/209; A61M 11/02; A61M 11/06; A61M 15/0086; A61M 15/08; A61M 16/06; A61M 16/0666; A61M 16/0816; A61M 16/14; A61M 11/002; A61M 16/0833; A61M 16/208; A61M 2205/0233; A61M 2205/0238; A61M 2205/583; A61M 2207/00; A61M 2207/10; A61M 2209/06; A61M 2210/0618; A61M 2210/1007; A61M 2240/00; A61J 17/001; A61J 9/00

See application file for complete search history.

(56) References Cited

U.S. PATENT DOCUMENTS

| | | | |
|---|---|---|---|
| 5,427,089 A | 6/1995 | Kraemer | |
| 5,592,935 A * | 1/1997 | Elstran | A62B 7/02 128/205.25 |
| 5,598,835 A * | 2/1997 | von Schrader | A61M 15/00 128/200.14 |
| 5,685,291 A * | 11/1997 | Marsh | A61M 15/0086 128/200.15 |
| 5,848,587 A * | 12/1998 | King | A61M 15/0086 128/200.18 |
| 5,904,140 A | 5/1999 | McGoogan | |
| 5,988,160 A * | 11/1999 | Foley | A61M 15/00 128/200.14 |
| 6,012,455 A * | 1/2000 | Goldstein | A61M 16/0488 128/204.18 |
| 6,014,972 A * | 1/2000 | Sladek | A61M 15/0065 128/203.12 |
| 6,336,453 B1 | 1/2002 | Scarrott et al. | |
| 6,336,455 B1 | 1/2002 | Howlett | |
| 6,394,085 B1 | 5/2002 | Hardy | |
| 6,412,481 B1 * | 7/2002 | Bienvenu | A61M 15/0086 128/200.21 |
| 6,412,488 B1 | 7/2002 | Barnett | |
| 6,470,882 B1 | 10/2002 | Newhouse et al. | |
| 6,557,548 B1 | 5/2003 | Dickson | |
| 6,578,571 B1 * | 6/2003 | Watt | A61M 15/00 128/200.14 |
| 6,615,824 B2 * | 9/2003 | Power | A61M 15/0085 128/200.14 |
| 6,626,168 B1 | 9/2003 | Carroll et al. | |
| 6,725,858 B2 * | 4/2004 | Loescher | A61M 16/08 128/200.14 |
| 6,789,543 B2 | 9/2004 | Cannon | |
| 6,904,908 B2 | 6/2005 | Bruce et al. | |
| 7,204,245 B2 | 4/2007 | Johnson | |
| 7,318,433 B2 | 1/2008 | Cockerham | |
| 7,360,537 B2 | 4/2008 | Snyder et al. | |
| 7,905,228 B2 * | 3/2011 | Blacker | A61M 11/06 128/200.14 |
| 8,122,881 B2 | 2/2012 | Giroux | |
| 8,151,794 B2 | 4/2012 | Meyer et al. | |
| 8,225,785 B2 * | 7/2012 | Richards | A61M 16/08 128/204.12 |
| D754,845 S | 4/2016 | Duran | |
| 9,700,688 B2 | 7/2017 | Engelbreth | |
| 2002/0112724 A1 | 8/2002 | Newhouse | |
| 2005/0039746 A1 * | 2/2005 | Grychowski | A61M 15/0086 128/204.18 |
| 2006/0254479 A1 | 11/2006 | Luchetti et al. | |
| 2007/0000495 A1 | 1/2007 | Matula, Jr. et al. | |
| 2010/0000525 A1 | 1/2010 | Lee | |
| 2010/0101570 A1 | 4/2010 | Meyer et al. | |
| 2010/0147298 A1 | 6/2010 | Loescher et al. | |
| 2012/0285236 A1 | 11/2012 | Haartsen et al. | |
| 2012/0291779 A1 | 11/2012 | Haartsen et al. | |
| 2012/0318261 A1 | 12/2012 | Newhouse et al. | |
| 2012/0318265 A1 | 12/2012 | Amirav et al. | |
| 2013/0008436 A1 | 1/2013 | Vol Hollen et al. | |
| 2013/0025594 A1 | 1/2013 | Wachtel et al. | |
| 2017/0173281 A1 | 6/2017 | Engelbreth | |

* cited by examiner

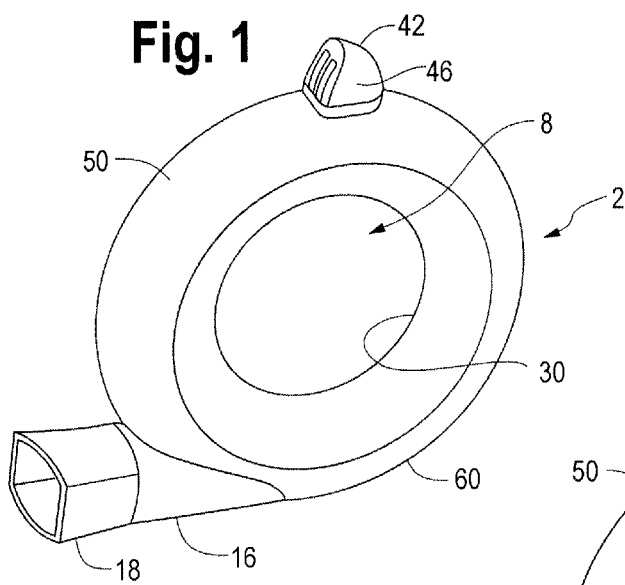
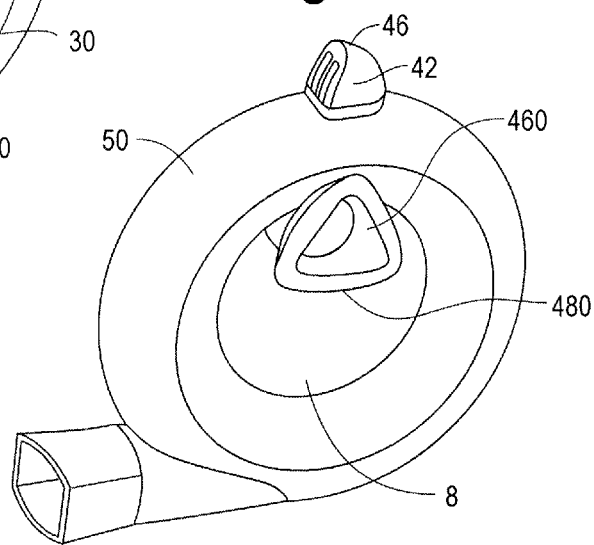
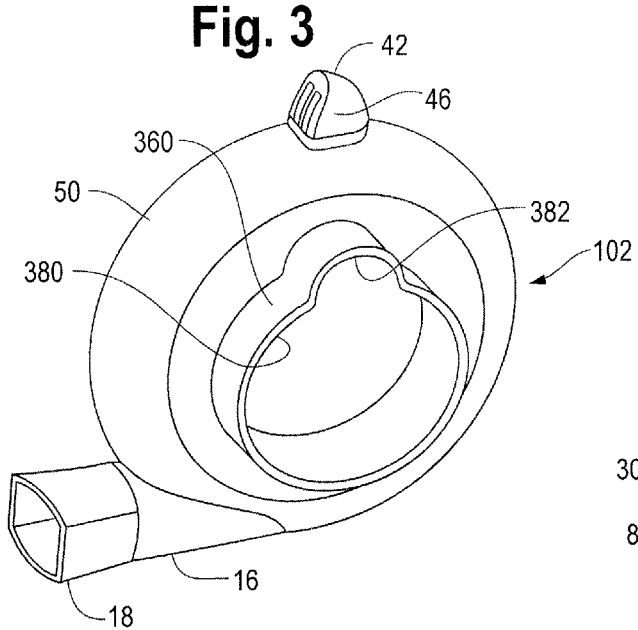
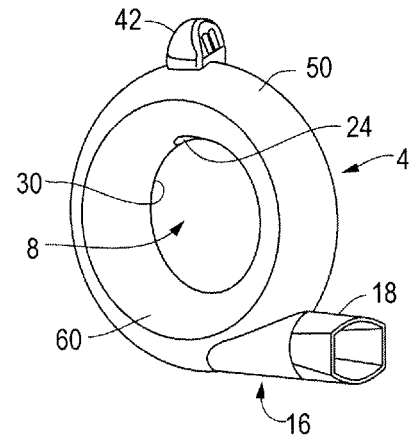

INHALATION FLOW
EXHALATION FLOW

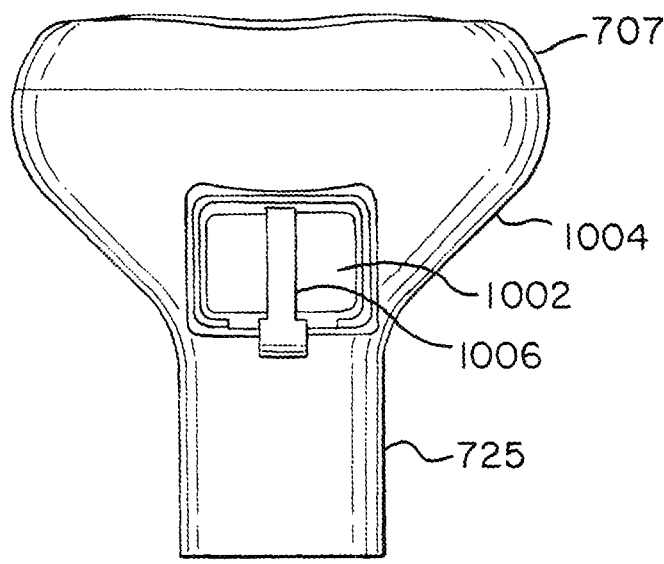
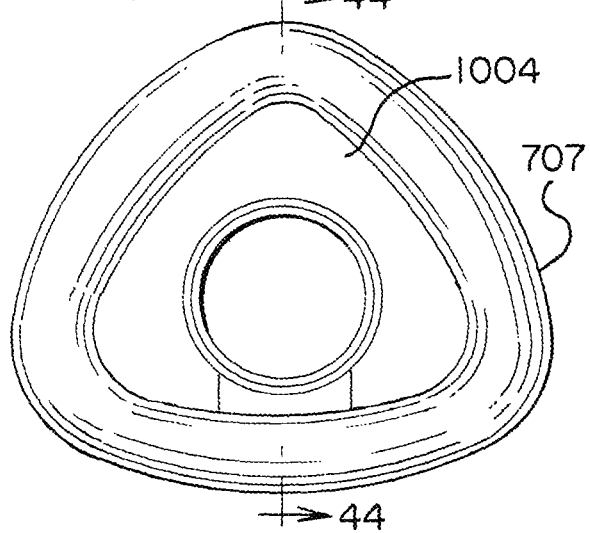
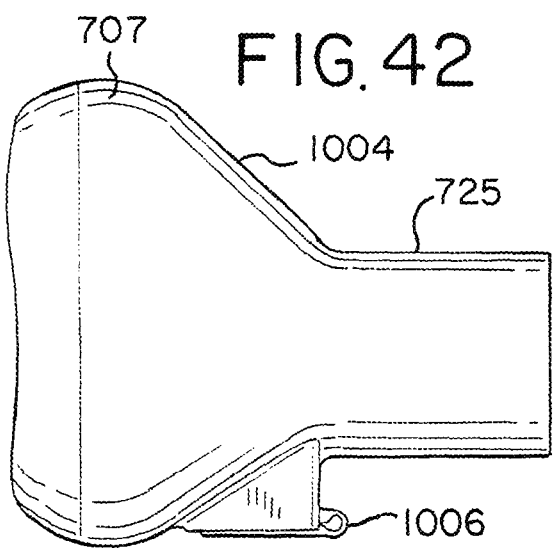
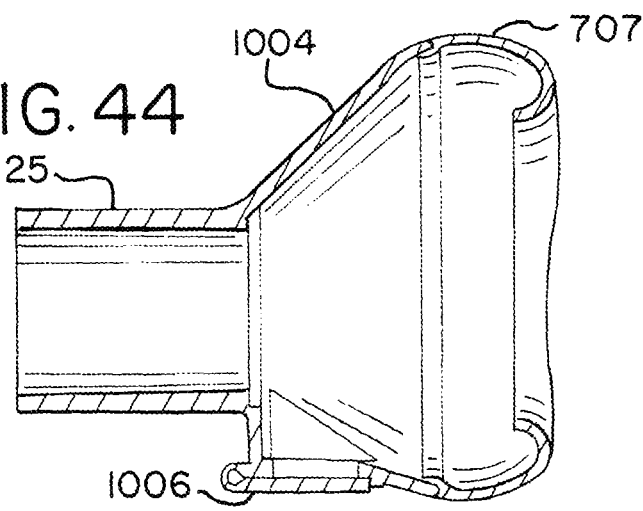

DELIVERY DEVICE AND KIT, AND METHOD OF USE

This application is a continuation of International Application PCT/IB2014/000360, filed Mar. 14, 2014, which application claims the benefit of U.S. Provisional Application No. 61/792,583, filed Mar. 15, 2013, U.S. Provisional Application No. 61/878,384, filed Sep. 16, 2013, and U.S. Provisional Application No. 61/904,765, filed Nov. 15, 2013, the entire disclosures of which are hereby incorporated herein by reference.

TECHNICAL FIELD

The present invention relates generally to a delivery device, including an aerosol delivery device suitable for delivering an aerosolized substance, such as a medicament, to the lungs of a patient, such as an infant, for example to the nasal cavities of an infant while being soothed orally, and also to aerosol delivery kits and methods of delivering aerosol medicament or the like.

BACKGROUND

It is well known to deliver aerosolized medicaments to a patient via various devices, including nebulizers and aerosol dispensing devices, such as pressurized Metered Dose Inhalers (PMDI's), in order to treat various conditions and diseases, including but not limited to various respiratory conditions and diseases such as asthma. For example, premature babies, termed neonate or pre-term babies, are often born with underdeveloped lungs and may be prone to lung infections such as pneumonia. Preterm babies also may suffer from respiratory distress syndrome (RDS), wherein their lungs lack a surfactant necessary to prevent the air sacks from collapsing, leading to breathing difficulties.

Along with delivery of aerosolized medication directly to targeted areas within the lungs, it may also be desirable to deliver certain gases, such as oxygen, or vapor of a substance, such an aromatic substance, to a patient having difficulty breathing. In some configurations, the device is configured with a patient interface mouthpiece, which is inserted into the mouth of a user such that the aerosolized medicament can be inhaled into the lungs of the user. In other embodiments, the patient interface is configured as a mask, which typically is fitted around the nose and mouth of the user so as to maximize and ensure inhalation of the aerosolized medicament into the lungs of the user.

These types of patient interfaces may not be ideally suited for certain patients, however, such as infants. Infants may tend to reject having a mask positioned over their face and thereby covering their nose and mouth. The infant may become cranky, irritable and prone to crying, which reduces the likelihood of delivering a proper amount of the desired substance, such as a medicament.

In addition, infants up to the age of 18 months are primarily nose breathers. With such patients, the mouth rarely has a role in inhalation except in situations where there is a complete occlusion of the nasal passageways. Moreover, infants are not capable of understanding and/or following instructions to inhale only through their mouth, e.g., if a mouthpiece is introduced therein, and the likelihood of delivering the proper amount of medicament is greatly reduced with such a device. As such, a need remains for an improved device capable of delivering an aerosolized medicament, gas, or other desired substance to the nasal passageways of a patient, particularly infants, without causing anxiety and distress to the patient.

Neonates also have very delicate skin, which may be susceptible to irritation, abrasion and other potential damage when engaged by a non-pliable mask, made for example from hard plastic or with relative thick walls. Conversely, masks made entirely of silicone or soft polymer may be susceptible to buckling or collapse if made with thin walls, which may have a negative impact on aerosol delivery. As such, a need remains for an improved mask for use with users, such as neonates, having sensitive skin, even when covering either or both of the mouth or nose of the user.

SUMMARY

Briefly stated, in one aspect, one embodiment of a delivery device includes a toroidal shaped housing defining an interior chamber and a central open space. The housing includes an input port communicating with the interior chamber and a delivery port positioned on an inner periphery of the housing. The delivery port is in fluid communication between the interior chamber and the central open space. The delivery port is spaced from the input port, which is adapted to receive an aerosolized medicament.

In another aspect, one embodiment of a delivery device kit includes an outer ring-like housing component defining at least in part a holding chamber and having an input port communicating with the holding chamber. A first inner ring-like housing component defines at least in part a first holding chamber and a first central through opening shaped to matingly receive at least a portion of a breast. The first inner ring-like housing component includes a first delivery port. The first inner ring-like housing component and the outer ring-like component are configured for mateable coupling to define a first enclosed holding chamber. A second inner ring-like housing component defines at least in part a second holding chamber and a central open space. The second inner ring-like housing component includes a second delivery port. The second inner ring-like housing component and the outer ring-like component are configured for mateable coupling to define a second enclosed holding chamber. The second inner ring-like housing includes a soother device extending into the central open space. A third inner ring-like housing component defines at least in part a third holding chamber and a second central through opening. The third inner ring-like housing component includes a third delivery port. The third inner ring-like housing component and the outer ring-like component are configured for mateable coupling to define a third enclosed holding chamber. The third inner ring-like housing has an annular wall defining the second central through opening. The annular wall is shaped to matingly receive and seal against a bottle extending into the second central through opening.

In another embodiment, a delivery device kit includes an outer ring-like housing component defining at least in part a first cavity and having an input port communicating with the first cavity. A plurality of inner ring-like housing components each define at least in part a second cavity, a central space, and a delivery port, wherein each of the inner ring-like housing components is configured to individually mate with the outer ring-like component such that the first and second cavities define an enclosed holding chamber. Each of the inner ring-like housing components includes a user side and a provider side, wherein at least one of the user side or provider side of each of the plurality of inner ring-like housing components is configured differently from the user side or provider side of others of the plurality of inner ring-like housing components.

In another aspect, one embodiment of a method of delivering an aerosolized medicament includes positioning a nose and a mouth of a user in a central opening defined by a ring-like housing, introducing an aerosolized medicament through an input port into an interior chamber defined by the ring-like housing and inhaling through the nose and thereby drawing the aerosolized medicament from the interior chamber into the central opening through a delivery port disposed on an inner periphery of the ring-like housing. The method further includes exhaling through the nose into the central opening and soothing the user by positioning a soothing device located in the central opening in the mouth of the user during said inhaling and exhaling. The soothing device, for example, may be one of a nipple extending from a breast, a bottle or a pacifier.

In another aspect, a delivery device includes a holding chamber having an input end and an output end and a nasal mask coupled to the output end. The nasal mask has a bottom flexible edge portion and a pair of flexible side portions. The side portions extend upwardly from the bottom portion and connect at an apex. In one embodiment, the mask includes a flexible sealing portion defining the bottom and side portions. The sealing portion may be coupled to a mounting portion, which is adapted to be coupled to the output end of the holding chamber. In one embodiment the sealing portion and mounting portion are formed by overmolding the components, for example in a two-shot molding process. The sealing portion may be made of a soft polymer, while the mounting portion may be made of a hard plastic. The sealing portion is shaped to define a cavity to receive the user's nose, but with the mouth of the user accessible and open to the ambient environment below the sealing portion, allowing access for example of a soothing device.

In another aspect, one embodiment of a delivery device includes a substance dispenser and a mask in fluid communication with the substance dispenser. The mask includes a mounting portion comprising a hard plastic coupled to a sealing portion comprising a soft polymer.

In yet another aspect, one embodiment of a delivery device includes a mask having a mounting portion made at least in part of a hard plastic coupled to a sealing portion made at least in part of a soft polymer. An adapter is connected to the mounting portion of said mask. The adapter includes a relief valve. In various embodiments, the adapter may also include a separator, a gravity chamber and/or a baffle.

The various aspects and embodiments provide significant advantages over other delivery devices, kits and methods. Typically, an infant will remain calm, and continue with a regular and uninterrupted breathing cycle, when being soothed orally, for example by nursing, feeding from a bottle or sucking on a pacifier. As such, breathing is not compromised when the infant is nursing, feeding or sucking on a pacifier. The present embodiments facilitate the administration to an infant of an aerosolized medicament from a nebulizer, pressurized metered dose inhaler ("pMDI") or other aerosol dispensing device. The embodiments allow a caregiver to deliver an aerosolized medicament to the nasal passageways of the user while allowing and providing for the user to nurse, feed, suck or otherwise be soothed during the delivery sequence. In addition, the modular construction of the device, with a plurality of different patient soother interfaces provides the caregiver with a variety of choices to administer the medications. For example, in various public venues, or in other situations where nursing and/or feeding may not be convenient or practical, including hospital settings, the caregiver may use the pacifier soother interface to sooth the infant while delivering the medicament. The embodiments also can facilitate the delivery of gases, such as oxygen, or a desired substance in vapor form to the user for inhalation.

In addition, the configuration of the mask, with a rigid mounting portion and a flexible sealing portion provides a light touch to the user's face without compromising the ability to create a seal without collapsing the mask around the nose and/or mouth of the user. In certain embodiments, the relief valve may help to prevent a build-up of air pressure in the mask, such that the mask can be used with various substance dispensers such as a nebulizer. The shape and configuration of the adapters allows the user or caregiver to properly position and adjust the mask and nebulizer.

The present embodiments of the invention, together with further objects and advantages, will be best understood by reference to the following detailed description taken in conjunction with the accompanying drawings.

BRIEF DESCRIPTION OF THE DRAWINGS

FIG. 1 is a perspective view of one embodiment of a delivery device.

FIG. 2 is a perspective view of an alternative embodiment of a delivery device.

FIG. 3 is a perspective view of another alternative embodiment of a delivery device.

FIG. 4 is an opposite side perspective view of the embodiment of a delivery device shown in FIG. 1.

FIG. 5 is a top view of the delivery device shown in FIG. 4.

FIG. 6 is a first side view of the delivery device shown in FIG. 4.

FIG. 7 is a second side view of the delivery device shown in FIG. 4.

FIG. 8 is a front view of the delivery device shown in FIG. 4.

FIG. 9 is an exploded perspective view of the delivery device shown in FIG. 4.

FIG. 10 is a schematic side view of the delivery device shown in FIG. 4 during an inhalation sequence.

FIG. 11 is a schematic side view of the delivery device shown in FIG. 4 during an exhalation sequence.

FIG. 12 is a top, schematic side view of an infant nursing while using the delivery device shown in FIG. 4.

FIG. 13 is a perspective view of adelivery device kit having a plurality of patient soothing interfaces.

FIG. 14 is a perspective view of another alternative embodiment of a delivery device.

FIG. 15 is a perspective view of another alternative embodiment of a delivery device.

FIG. 16 is a side cross-sectional view of a user and provider with a delivery device disposed therebetween.

FIG. 17 is a side cross-sectional view of a user and a provider with an alternative embodiment of a delivery device disposed therebetween.

FIG. 18 is a perspective view of an alternative embodiment of a deliver device.

FIG. 19 is a cross-sectional view of the delivery device shown in FIG. 18.

FIGS. 20A-C show one embodiment of a nasal mask in perspective view, front view and cross-sectional view respectively.

FIG. 21 is a side view of the delivery device shown in FIG. 18 when in use with a patient, FIG. 22 is a perspective view of an alternative embodiment of a delivery device.

Figure 28A:
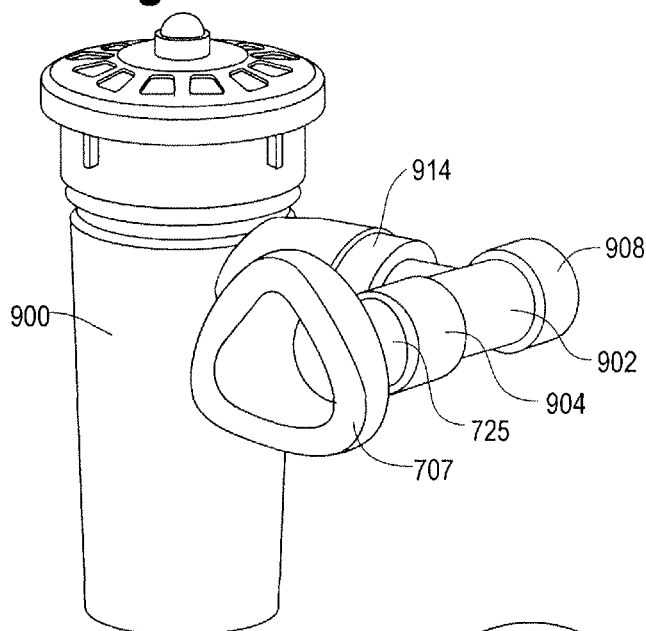
Figure 28B:
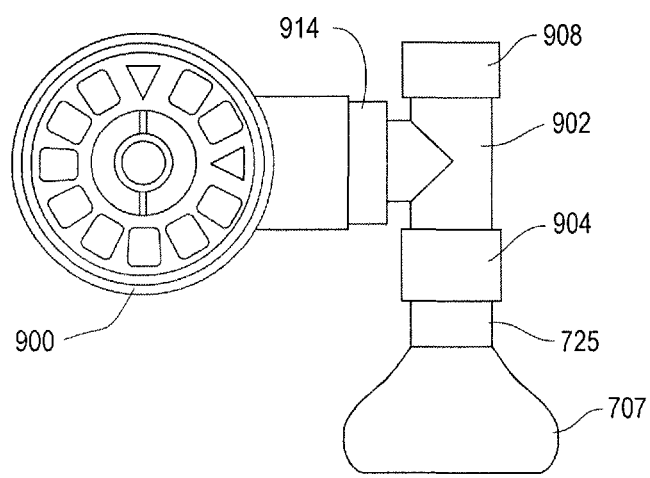
Figure 28C:
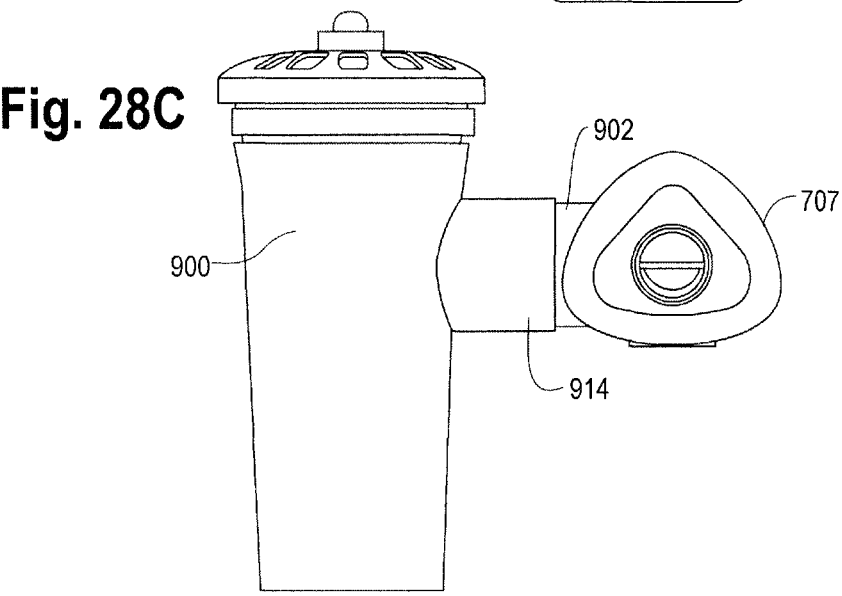

FIGS. 28A-C are perspective, top and front views of one embodiment of a delivery device including a mask, nebulizer and adapter.

Figure 29A:
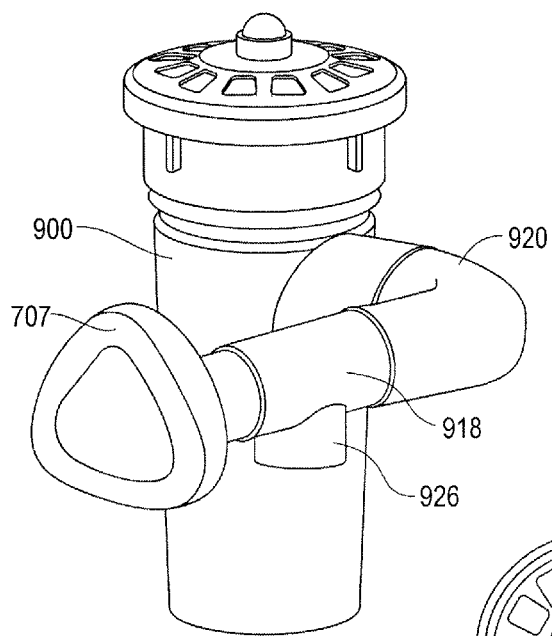
Figure 29B:
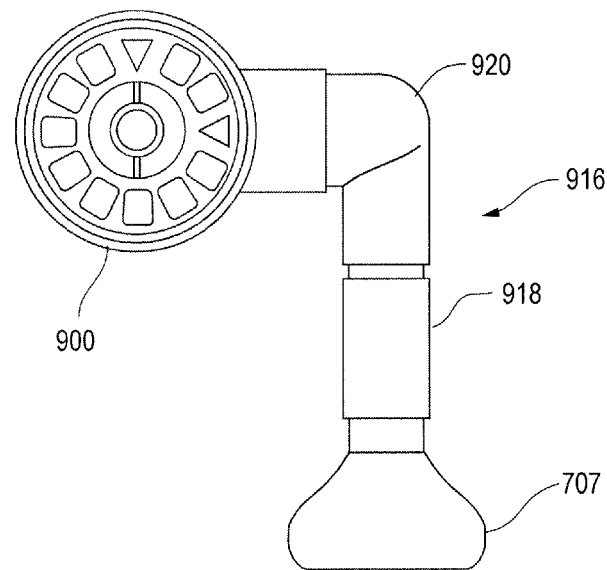
Figure 29C:
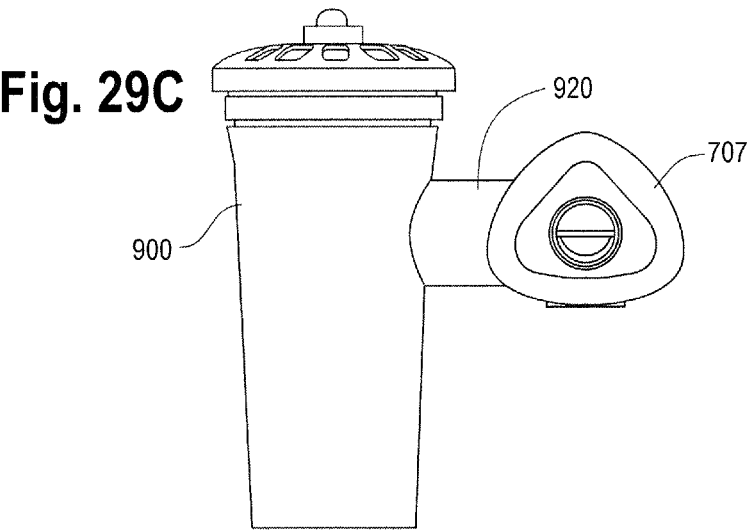

FIGS. 29A-C are perspective, top and front views of one embodiment of a delivery device including a mask, nebulizer and adapter.

Figure 30A:
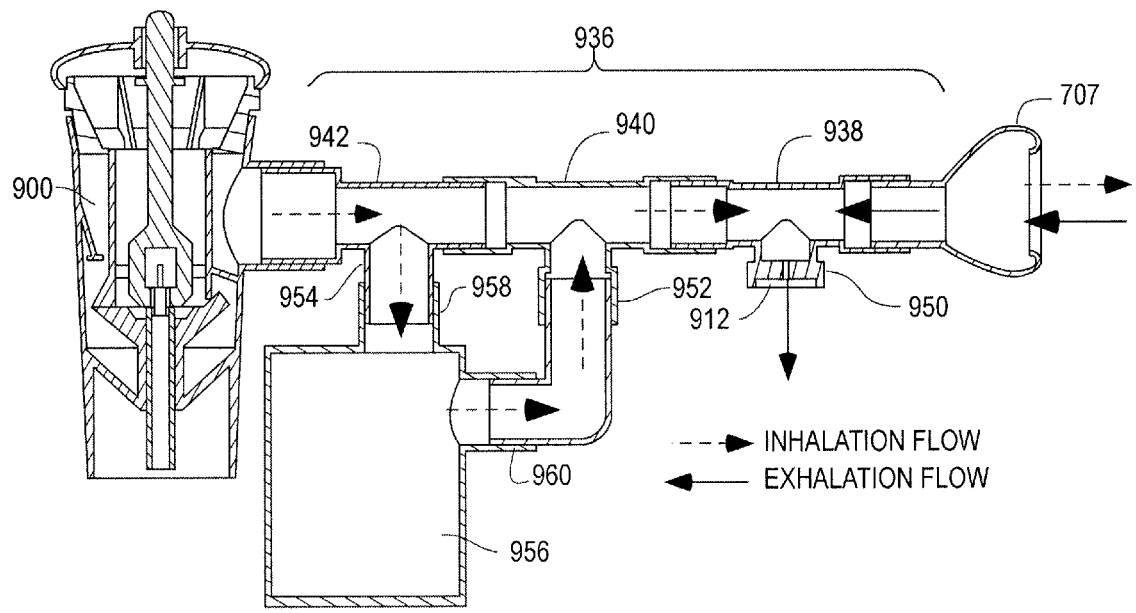
Figure 30B:
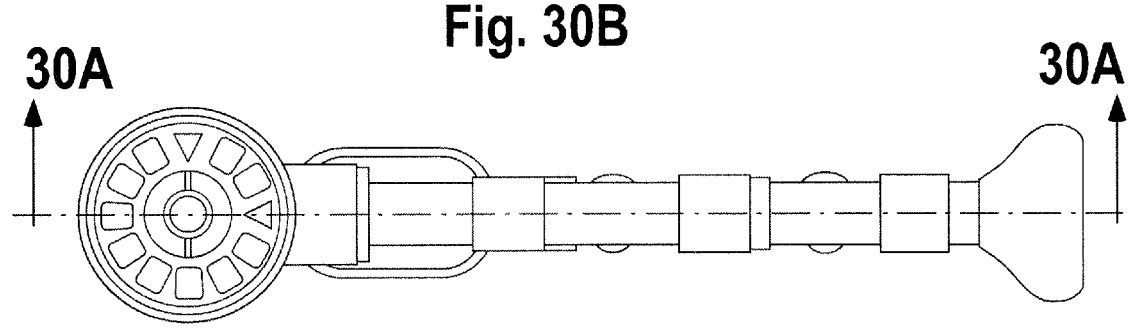

FIGS. 30A and B are cross-sectional and top views of another embodiment of a delivery device including a mask, nebulizer and adapter.

Figure 31A:
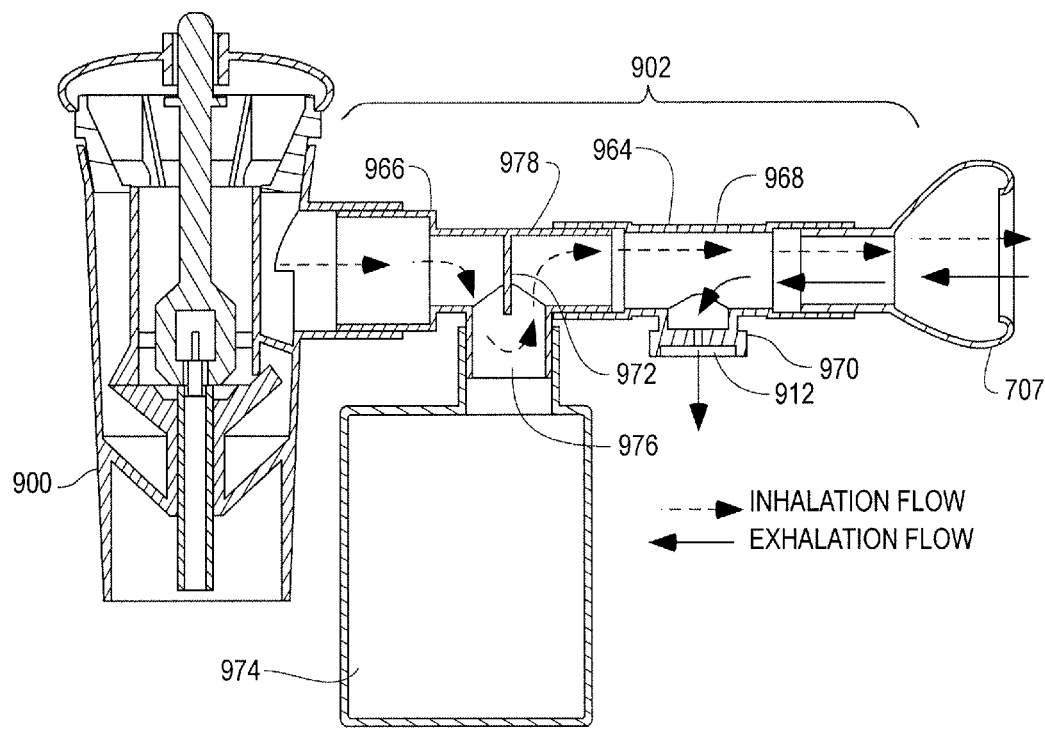

FIGS. 31A and B are cross-sectional and top views of another embodiment of a delivery device including a mask, nebulizer and adapter.

Figure 32:
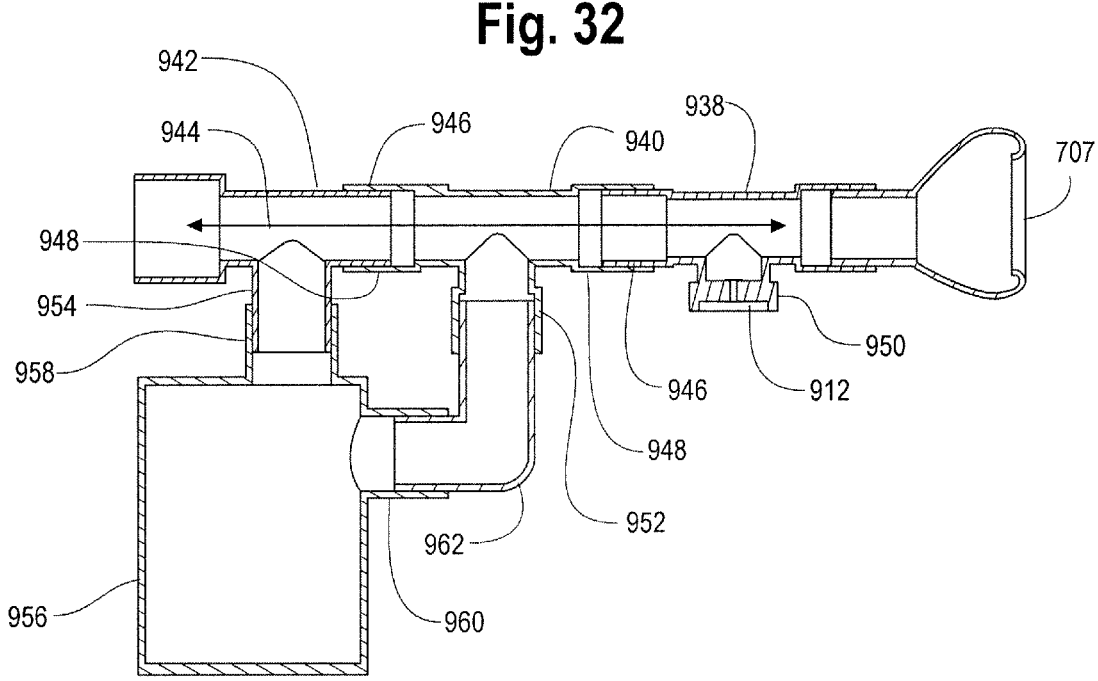

FIG. 32 is a cross-sectional view of the mask and adapter shown in FIG. 30A.

Figure 33:
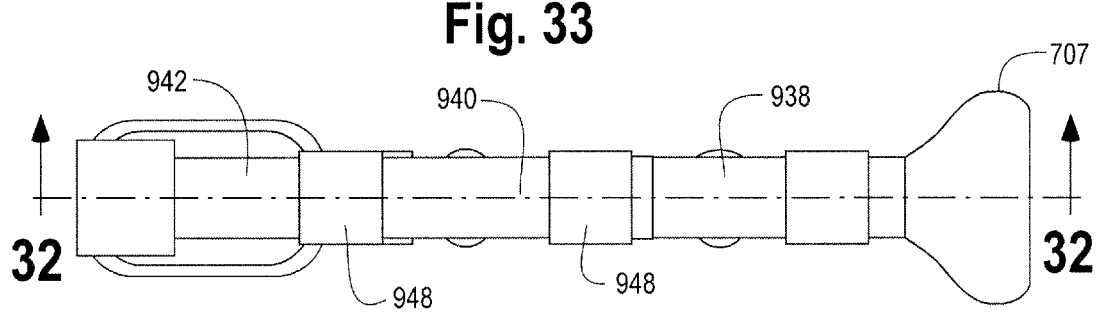

FIG. 33 is a side view of the mask and adapter shown in FIGS. 30A and 32.

Figure 34:
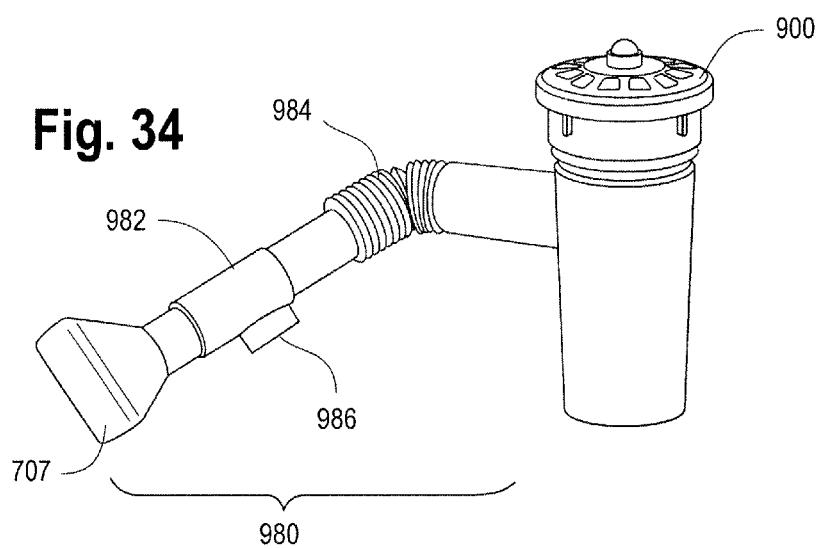

FIG. 34 is a perspective view of another embodiment of a delivery device including a mask, nebulizer and adapter.

Figure 35:
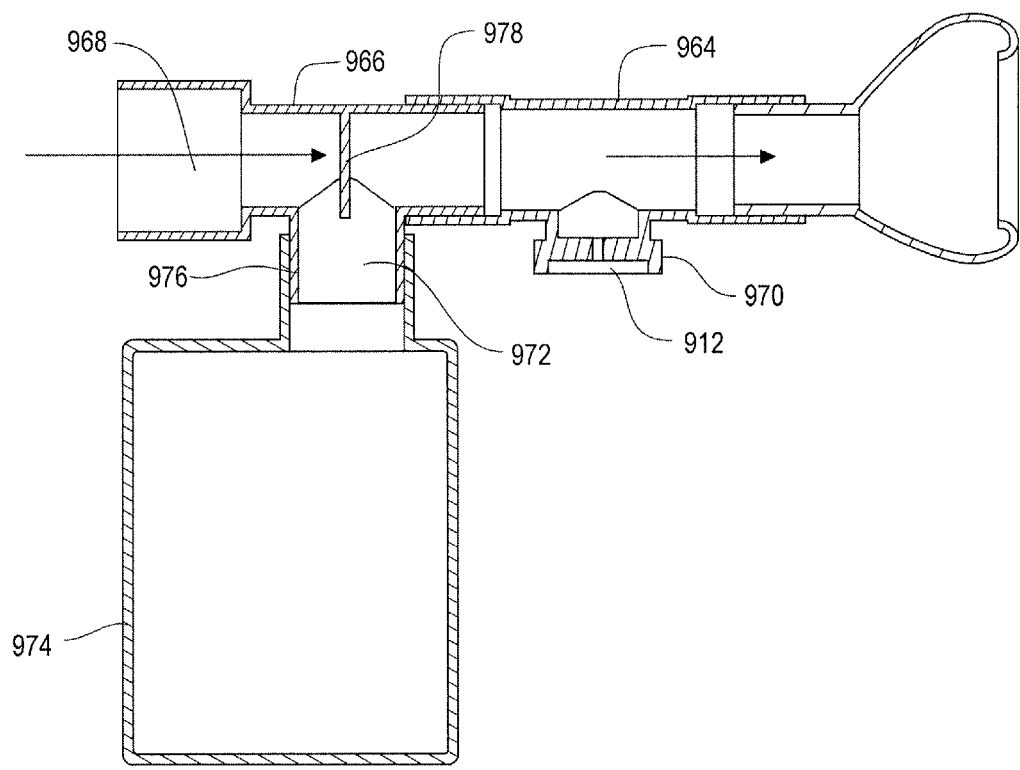

FIG. 35 shows a cross sectional view of the mask and adapter shown in FIG. 31A.

Figure 31B:
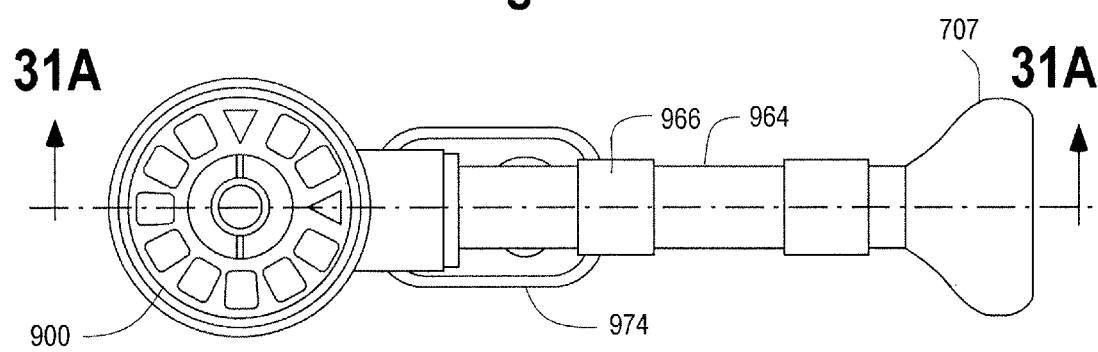
Figure 36:
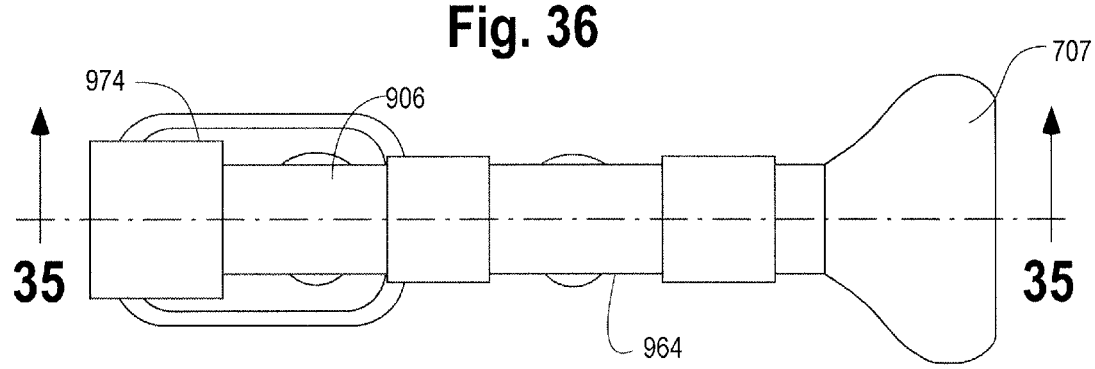

FIG. 36 shows a top view of the mask and adapter shown in FIG. 31B.

Figure 37:
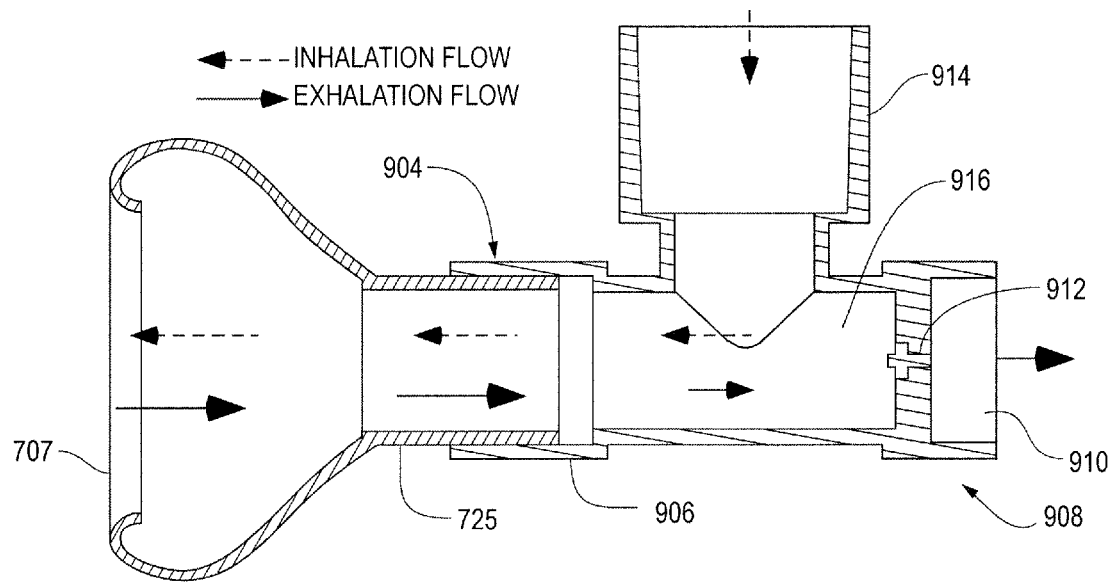

FIG. 37 is a cross-sectional view of the mask and adapter shown in FIG. 28A.

Figure 38:
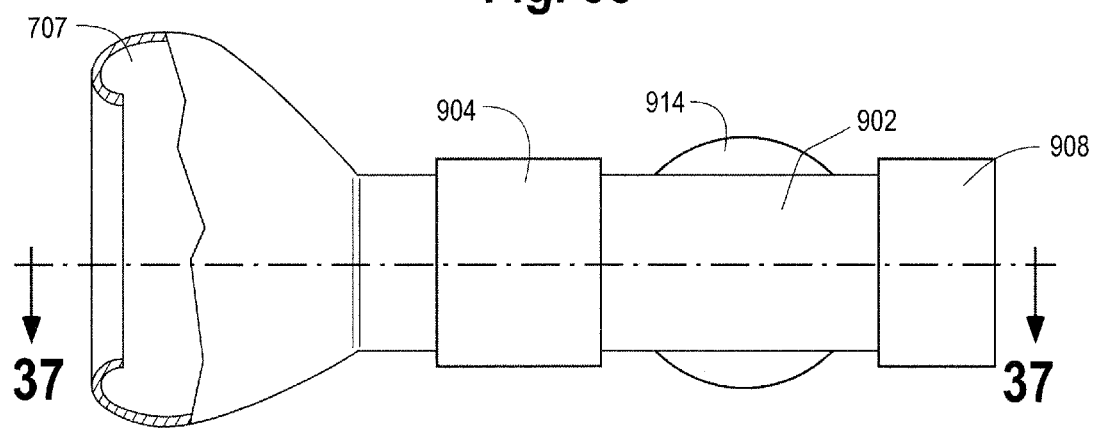

FIG. 38 is a side view of the mask and adapter shown in FIGS. 28A and 37.

Figure 39:
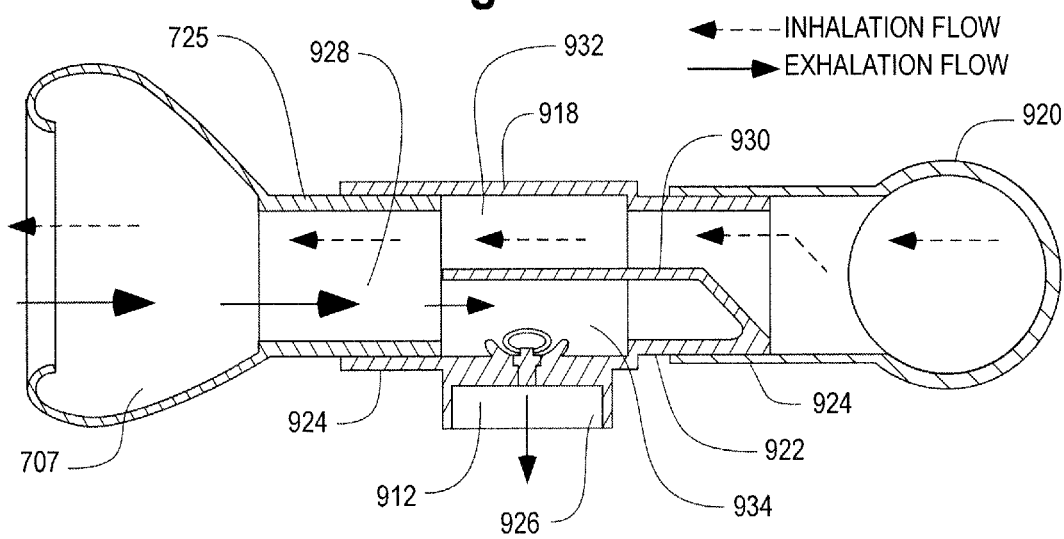

FIG. 39 is a cross-sectional view of the mask and adapter shown in FIG. 29A.

Figure 40:
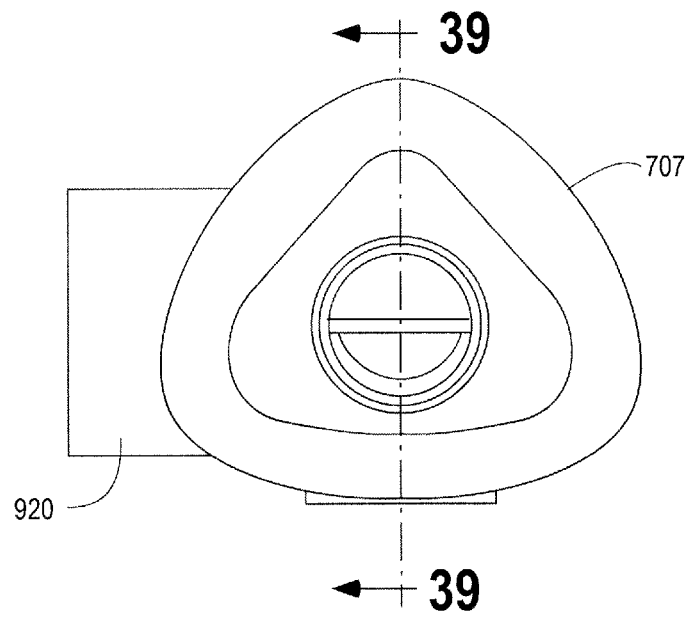

FIG. 40 is a side view of the mask and adapter shown in FIGS. 29A and 39.

Figure 45:
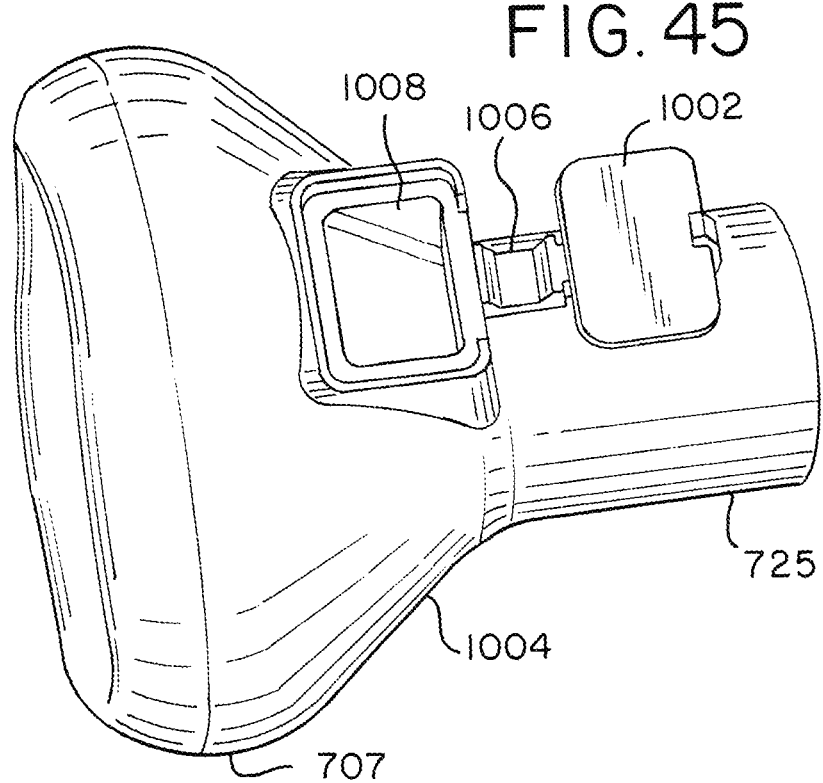
Figure 46:
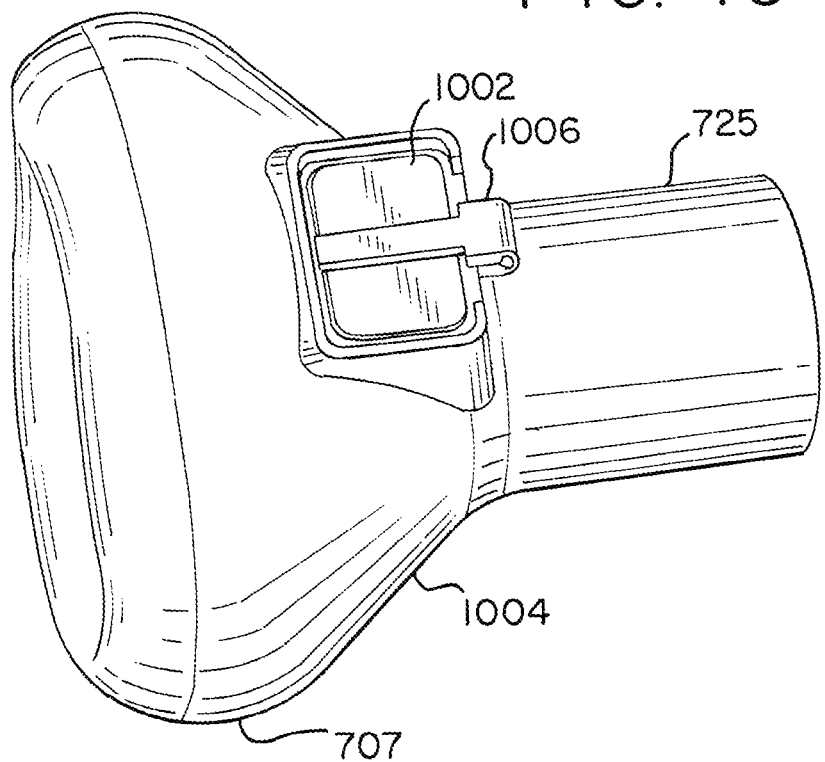

FIGS. 41-46 show various views of an alternative embodiment of a mask with a relief valve shown in a closed position (FIGS. 41-44 and 46) and an open position (FIG. 45).

Figure 47:
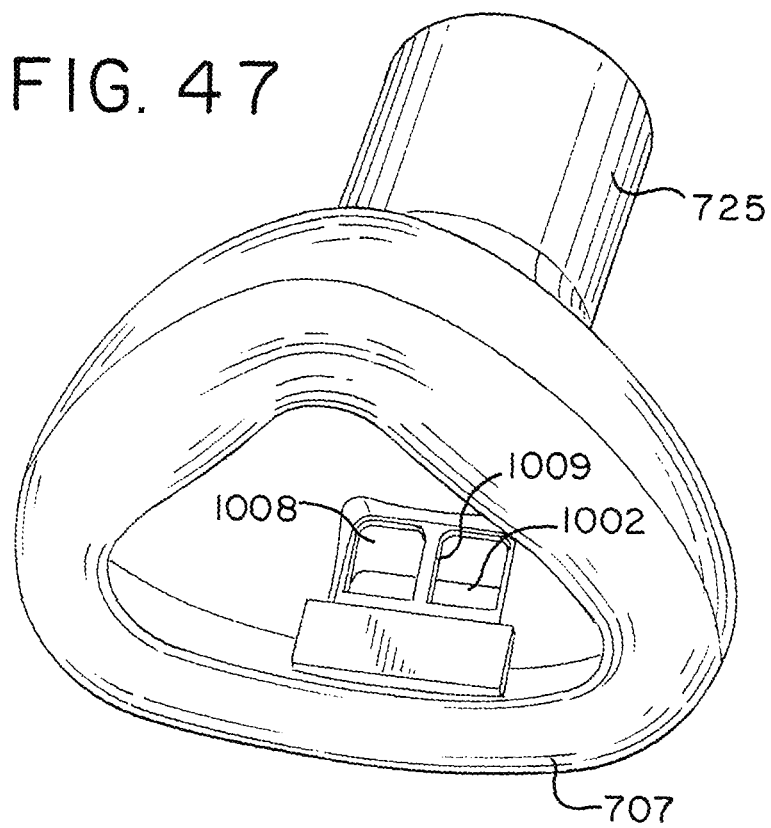
Figure 48:
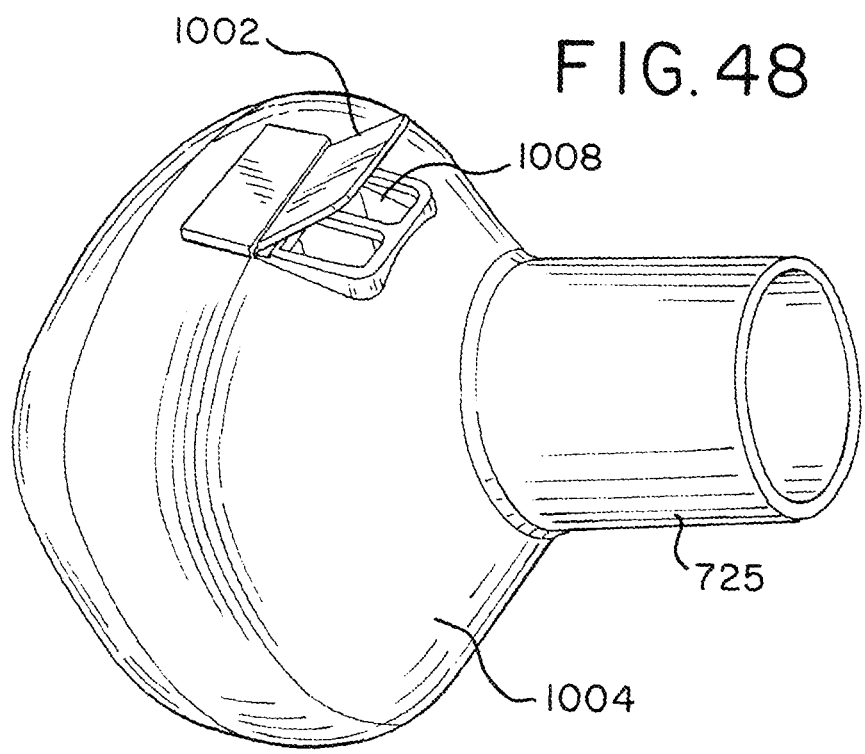

FIGS. 47 and 48 show perspective views of an alternative embodiment of a mask with a relief valve shown in a normally open position.

DETAILED DESCRIPTION OF THE PRESENTLY PREFERRED EMBODIMENTS

It should be understood that the term "plurality," as used herein, means two or more. The term "coupled" means connected to or engaged with, whether directly or indirectly, for example with an intervening member, and does not require the engagement to be fixed or permanent, although it may be fixed or permanent. It should be understood that the use of numerical terms "first," "second," "third," etc., as used herein does not refer to any particular sequence or order of components; for example "first" and "second" ring-like housing components may refer to any sequence of such members, and is not limited to the first and second ring-like housing components of a particular configuration unless otherwise specified. It should be understood that the terms "input port" and "delivery port" refer to the function of the ports during an inhalation phase, and that the delivery port may serve the opposite function (removal or exit) during an exhalation phase. It should be understood that the term "infant" as used herein refers to neonatal or pediatric patients and also includes children for whom a pacifier is comforting and useful for delivering aerosolized medication, gases or other therapeutic substance for inhalation.

Referring to FIGS. 1-3, 14 and 15, various embodiments of a delivery device are shown. In each of the embodiments, the delivery device includes a housing 2, 102, 202, 302, 402 defining an interior chamber 4. In one embodiment, the housing has a "toroidal" shape, defined as a surface generated by a geometric shape rotating about, but not intersecting or containing, an axis 6 in its own plane, or as a ring-like structure. For example and without limitation, the housing 2, 102, 202, 302, 402 may be substantially donut shaped, with a hollow interior, such as when the geometric shape, taken in cross section is a circle. In other embodiments, the cross-sectional shape may be an ellipse, a polygon, or a combination of curved and linear portions, whether closed or open. In addition, in some embodiments, the geometric shape may be rotated at constant radius "r" about the axis 6, e.g., thereby forming the donut shape with a circular central open space 8 or center opening, while in other embodiments the distance between the axis and the inner periphery may vary, for example by having an elliptically shaped central open space or opening, or defining some other shape such as an oval, obround, etc.

Figure 5:
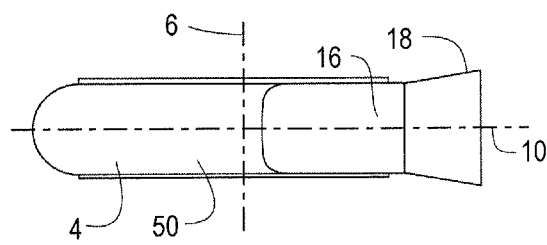
Figure 6:
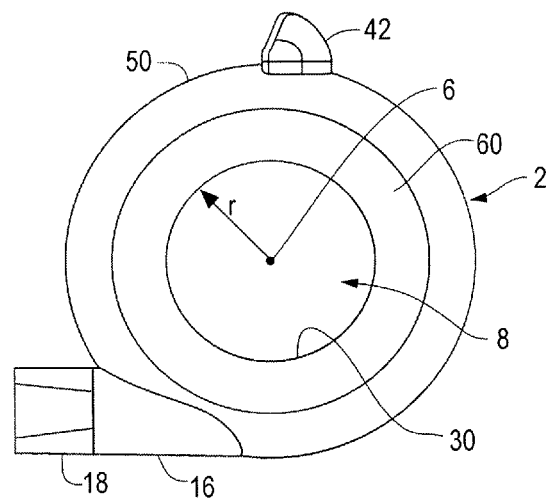
Figure 7:
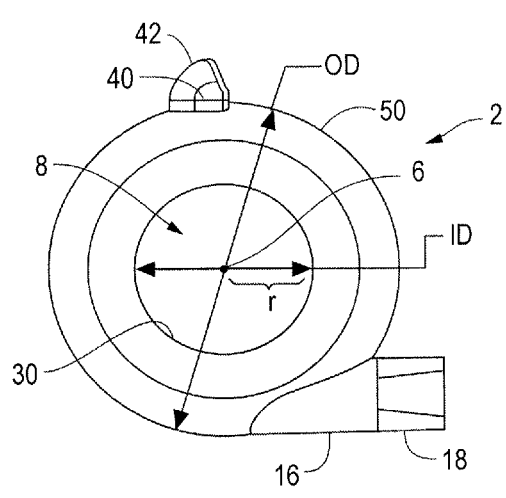
Figure 8:
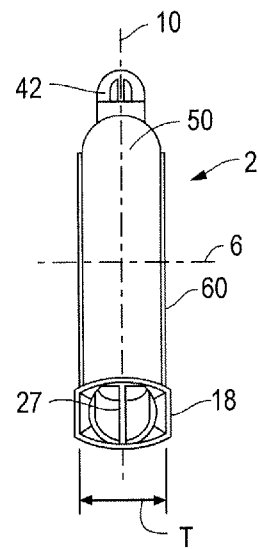

In the various embodiments shown, the housing is planar, and is centered on a plane 10 lying substantially perpendicular to the axis 6 defining the toroidal shape. In other embodiments, the housing may be non-planar. Referring to FIG. 8, the housing may be configured with various thicknesses (T) in the axial direction, for example from about 20 mm to about 60 mm, and in one embodiment from about 26 mm to about 50 mm. In this way, differently sized devices, e.g., small, medium and large, may be provided depending on the size and shape of the provider's breasts and size and shape of the head and/or face of the user. In the embodiments shown, the housing forms and defines the central open space 8, or central opening. In one embodiment as shown in FIGS. 6 and 7, wherein the central open space is circular, the inner diameter (ID) is from about 52 mm to about 75 mm. Again, differently sized openings may be provided depending on the size and shape of the provider's breasts and size and shape of the head and/or face of the user. Also in one embodiment, wherein the housing 4 is formed about the axis 6 at a constant radius "r", the outer diameter (OD) of the housing is from about 104 mm to about 130 mm.

Figure 9:
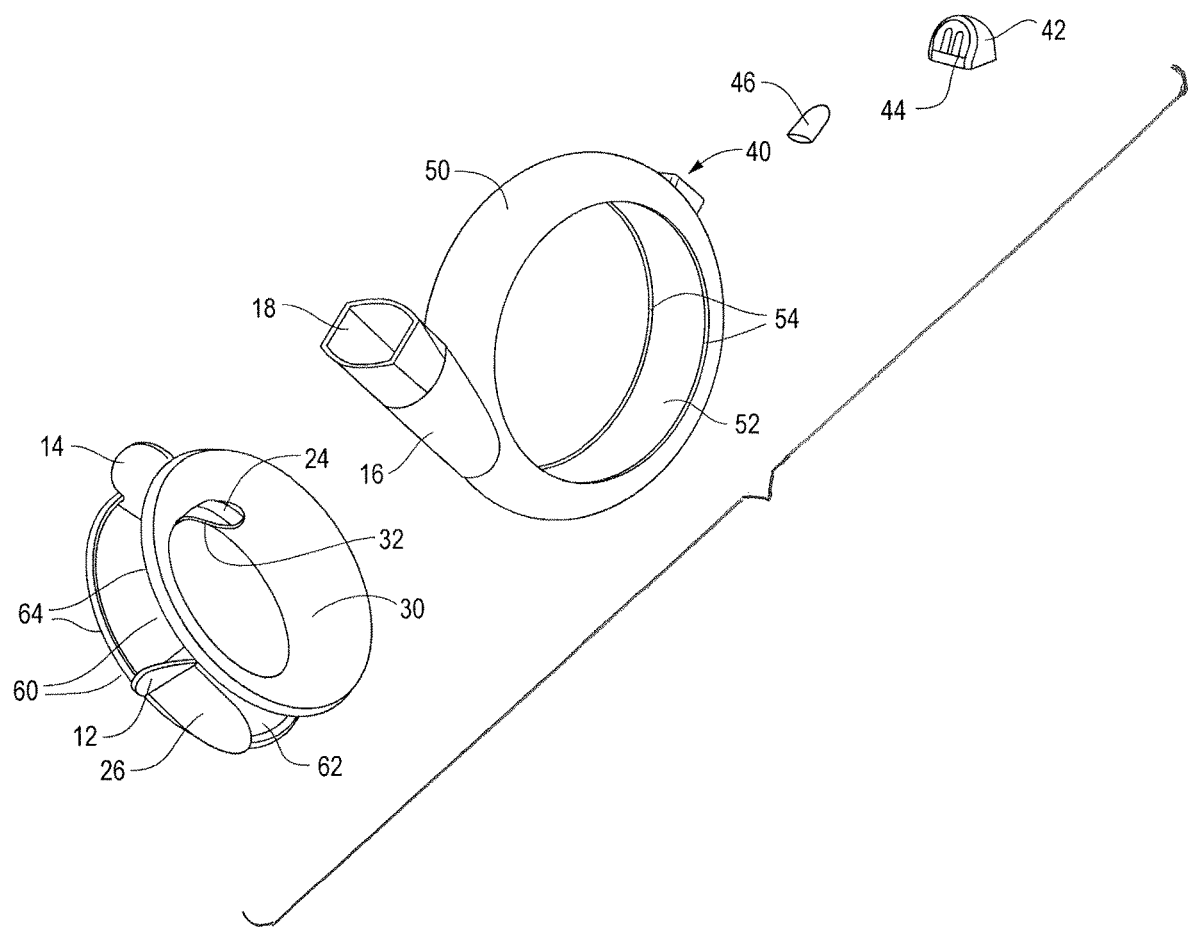
Figure 10:
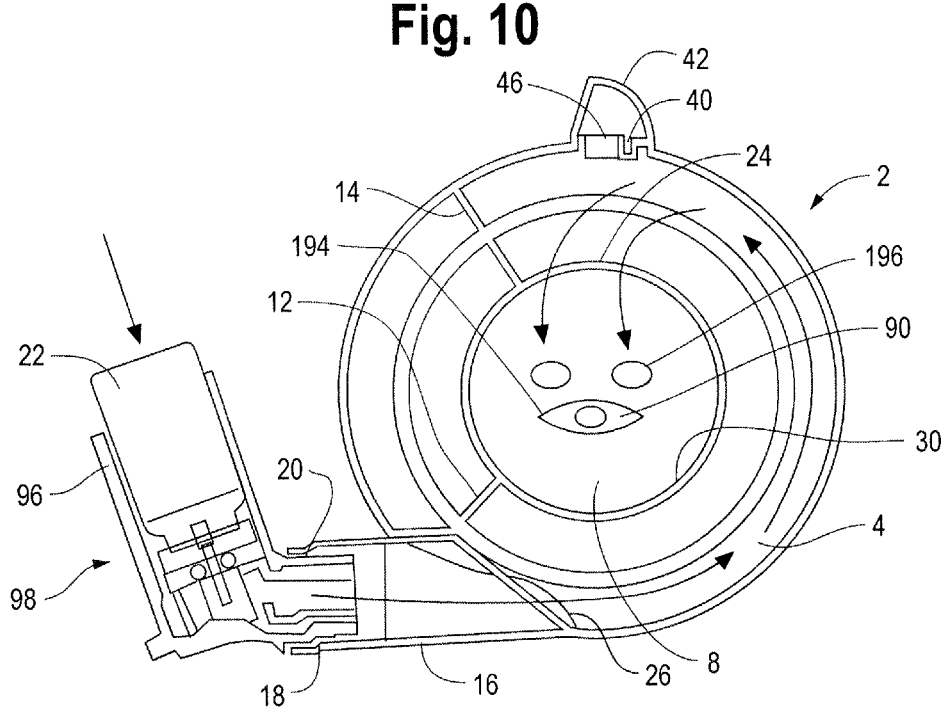
Figure 11:
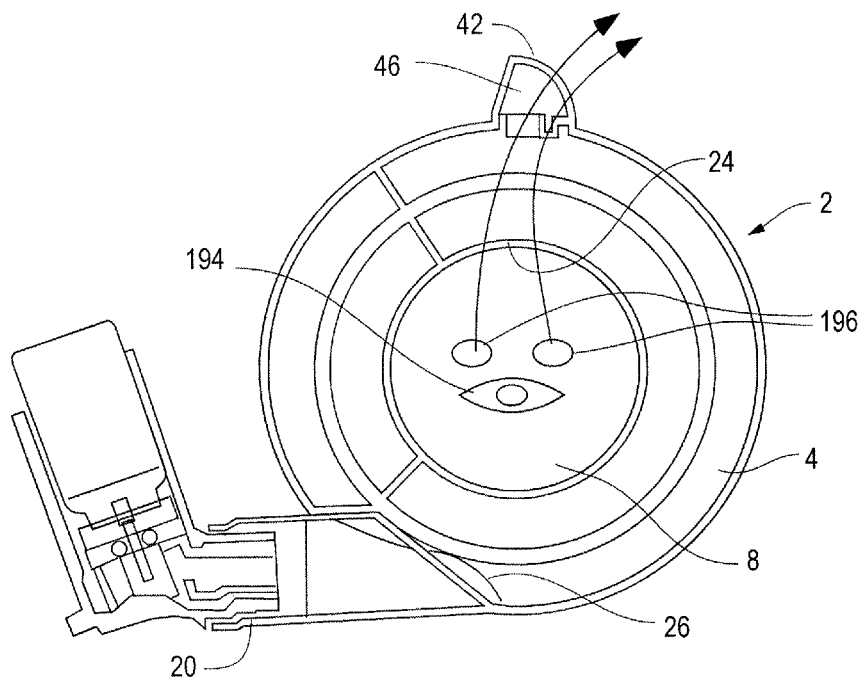

The interior chamber 4 may be formed around the entirety of the housing, or around only a portion thereof as shown for example in FIGS. 9-11, wherein a pair of walls 12, 14 close off a portion of the housing interior and define the interior chamber, thereby creating a flow path within the interior chamber. An input port 16 extends from the housing and is configured and shaped to receive a source of aerosolized medicament, for example a container 22 of medicament. For example, in one embodiment the input port includes a MDI boot portal 18, which is dimensioned and shaped to receive a mouthpiece portion 20 of an MDI actuator boot 96 as shown in FIGS. 10 and 11. The boot portal 18 may also be sized and shaped to receive a mouthpiece or output end of a valved holding chamber (VHC), spacer, nebulizer or other known aerosol delivery devices. The input port 16 may also be configured to receive tubing or other similar conduit suited to deliver oxygen or other gases or a vapor from a vapor emitter. The boot portal 18 may be made of a flexible material such as TPE or silicone, thereby allowing it to conform to and seal with differently shaped MDI, VHC, spacer or nebulizer output ends, such as mouthpieces 20.

In one embodiment, a one-way inhalation valve 26 is positioned adjacent to and covering an interior passageway of the input port 16, which is in fluid communication with the interior chamber 4. The one-way inhalation valve 26 may be configured as a flap valve, duckbill valve, center pin valve, or other known types of valves so as to allow a one-way flow of aerosolized medicament from a MDI container 22, VHC or other delivery device to the interior chamber 4. The input port 16 may have a grid 27 or valve seat disposed across the opening to prohibit access to the valve, while providing a surface for the valve, e.g., a flap valve, to seat against during an exhalation sequence.

At a second location spaced from the input port, a delivery port 24 is positioned on an inner periphery 30 of the housing 4 and is in fluid communication between the interior chamber 4 and the central open space 8. In various embodiments, a two-way valve may be positioned over the delivery port. The delivery port 24 may be formed as an opening in a wall of the housing 4, and may include one or more bars 32 or a grid-like structure to prevent the incursion of foreign bodies into or out of the delivery port. In some embodiments, a filter may be positioned over the delivery port.

At a third location, an exhalation port 40 is in fluid communication between the interior chamber 4 and the ambient environment outside of the central open space. For example, in one embodiment, the exhalation port 40 is positioned on an outer periphery 50 of the housing. A one-way exhalation valve 46, configured in various embodiments as a flap valve, duckbill valve, center pin valve, etc., is positioned adjacent the exhalation port 40 and permits a one-way fluid communication from the interior chamber 4 to the ambient environment. A shroud 42, shown as a curved clam-shell housing, surrounds and protects the valve. In one embodiment, the valve 46 is secured or trapped between the shroud 42 and housing 4, while in another embodiment, the valve 46 is coupled to the shroud, which in turn is connected to the housing, for example by a snap fit, etc. A bar or grid 44 may be formed across the opening of the shroud 42 to prevent access to the valve 46, and to provide a valve seat for the valve 46 to seat against during the exhalation sequence. The shroud may be made of a clear material such that the exhalation valve 46 is visible to a caregiver, which may monitor the position and movement of the exhalation valve 46 to determine and ensure the user is exhaling. In one embodiment, an indicator is used which provides a visual indication of when the infant is inhaling. The operation, construction and use of this type of inhalation visual indicator is further disclosed in U.S. Pat. No. 7,201,165, the entire disclosure of which is hereby incorporated herein by reference.

In various embodiments, the housing 4 is configured with an outer ring-like housing component 50 and an inner ring-like housing component 60, 160, 260, 360, 460. The outer ring-like housing component 50 forms and defines the input port 16 and exhalation port 40, while the inner ring-like housing components 60, 160, 260, 360, 460 each form and define the delivery port 24, the walls 12, 14 and the inhalation valve 26, all of which are integrally formed in one embodiment as shown in FIG. 9. In one embodiment, the outer ring-like housing component 50 is made of a relatively rigid material, such as a polymer based material or metal. The polymer based material may be made of or coated with various anti-static materials. In one embodiment, the outer ring-like housing component is made from an anti-static material, as disclosed for example and without limitation in U.S. Pat. No. 7,360,537, which is hereby incorporated herein by reference in its entirety. In one embodiment, the antistatic material, or coating applied to the housing, has a surface resistivity of less than about 10E12 ohm/sq., and preferably between about 10E10 and about 10E12 ohm/sq. Further examples of housings used in MDI ventilator assemblies are disclosed in U.S. Publication No. US 2005-39746A1 (entitled Ventilator Circuit and Method for the User Thereof), and U.S. Publication No. US 2006-0254479A1 (entitled Ventilator Circuit and Method for the User Thereof), the entire disclosures of which are hereby incorporated herein by reference.

Figure 17:
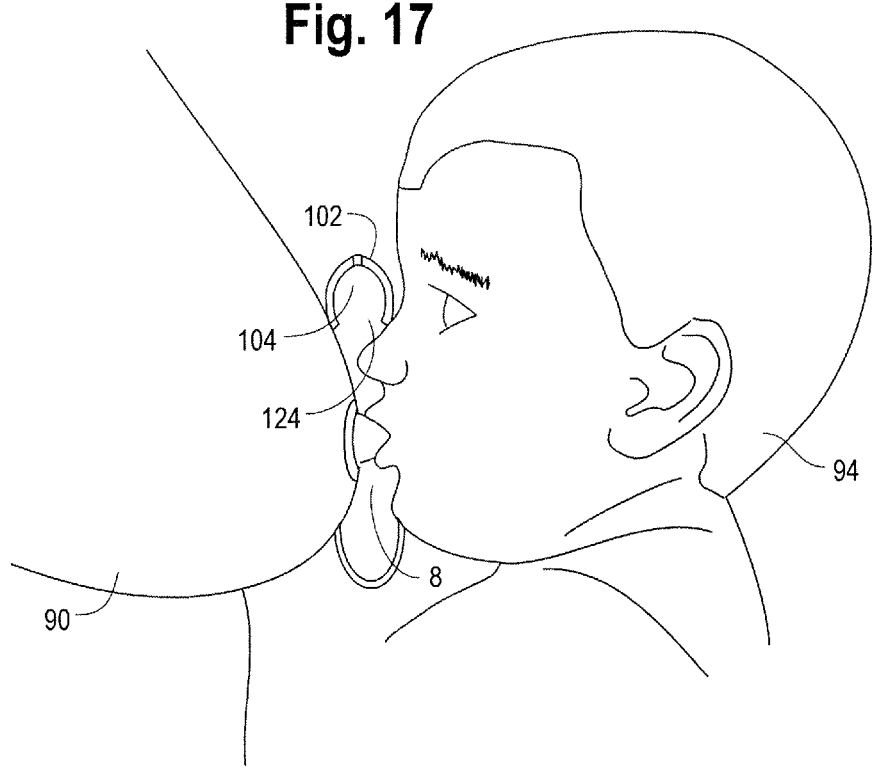
Figure 18:
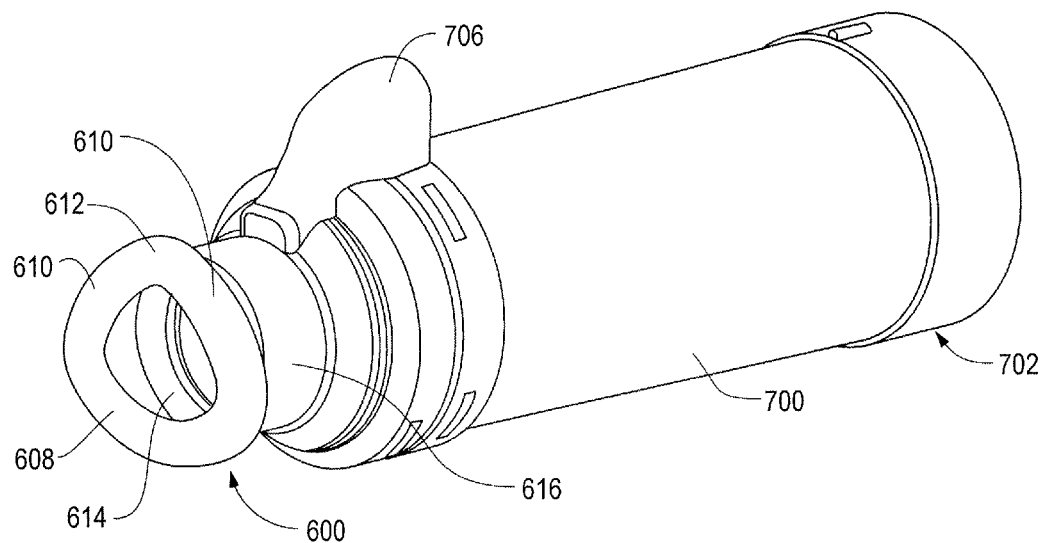
Figure 19:
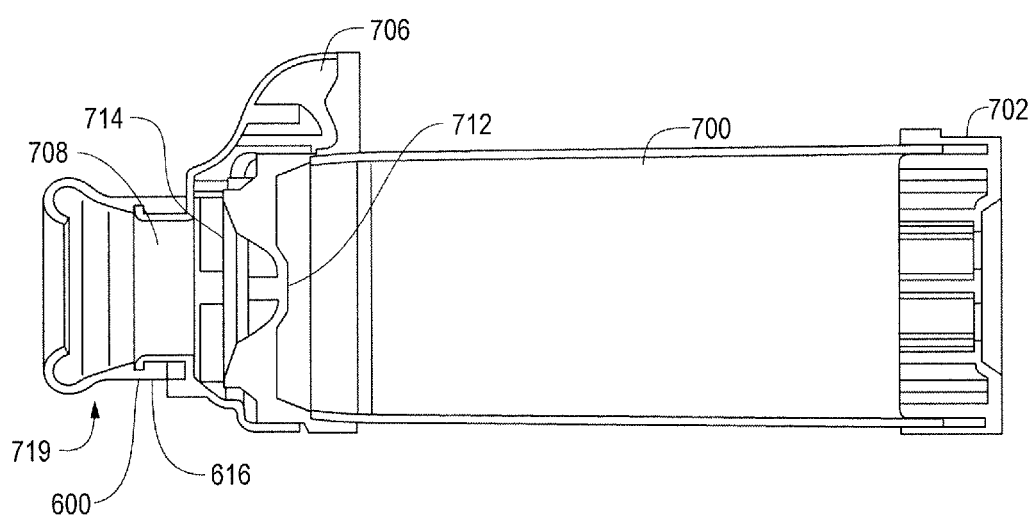
Figure 20A:
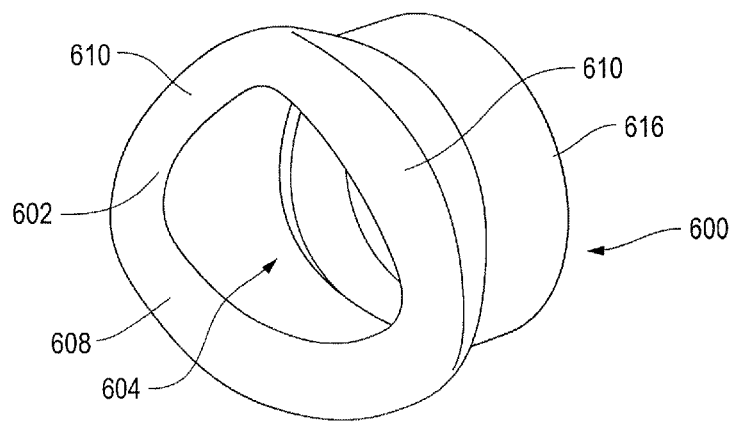
Figure 20B:
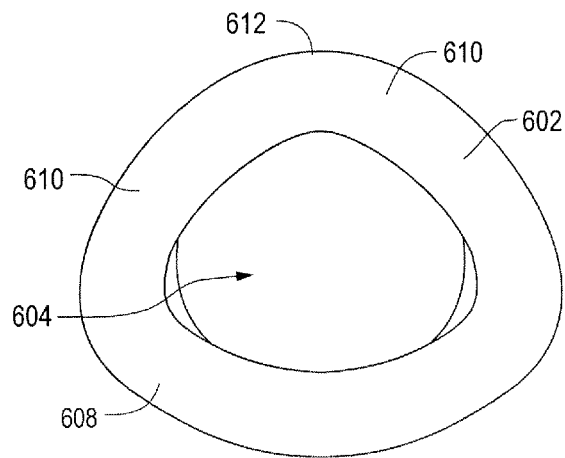
Figure 20C:
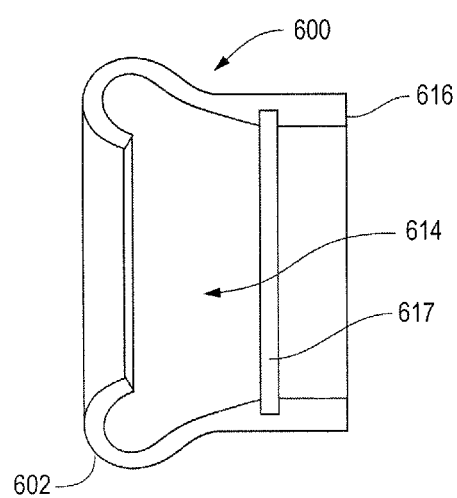

It should be understood that the housing may be integrally molded as a single ring-like housing component, for example made of silicone. In addition, as shown in FIG. 17, the inner peripheral wall of the housing may be left open, such that the cross-section of the entire housing 102 is C-shaped, with a provider side of the housing sealing again the provider and the use side sealing agains the face of the user, and with the interior chamber 104 opening along the inner periphery into the central opening 8. In this way, the mouth 124 of the C-shaped housing 102 defines the delivery portal. Notwithstanding that the cross-sectional shape is not a closed geometric shape, this embodiment is still considered to have a "toroidal" shape. In essence, the inner ring-like housing component may be omitted with an inhalation valve secured to the housing.

The inner ring-like housing component 60, 160, 260, 360, 460 is made of a relatively flexible, soft and resilient material, such as silicone, so as to provide a comfortable interface that more easily seals with the user's face on a user side of the device, and a caregiver's breast or bottle on an opposite provider side of the device. The outer ring-like housing component 50 and the inner ring-like housing component 60, 160, 260, 360, 460 each define in part a partial interior cavity 52, 62, or portion the interior chamber 4, and when joined, in combination define the interior chamber 4, which may function as a holding chamber, as shown in FIG. 9. The outer and inner ring-like housings 50, 60, 160, 260, 360, 460 may be joined by inner edges 54 of the outer ring-like housing interfacing with and fitting in annular grooves 64 formed in outer edges 66 of the inner ring-like housing. In other embodiments, the grooves may be formed on the outer ring-like housing, with the edges of the inner ring-like component interfacing therewith.

Figure 12:
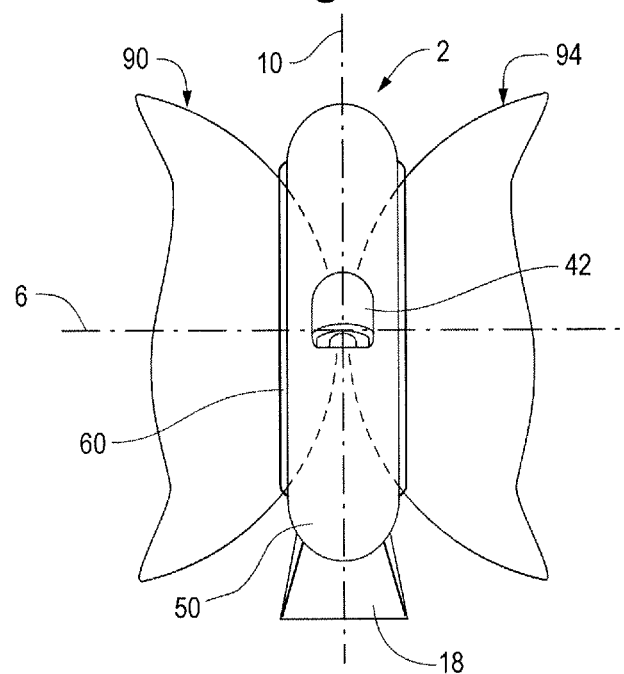
Figure 13:
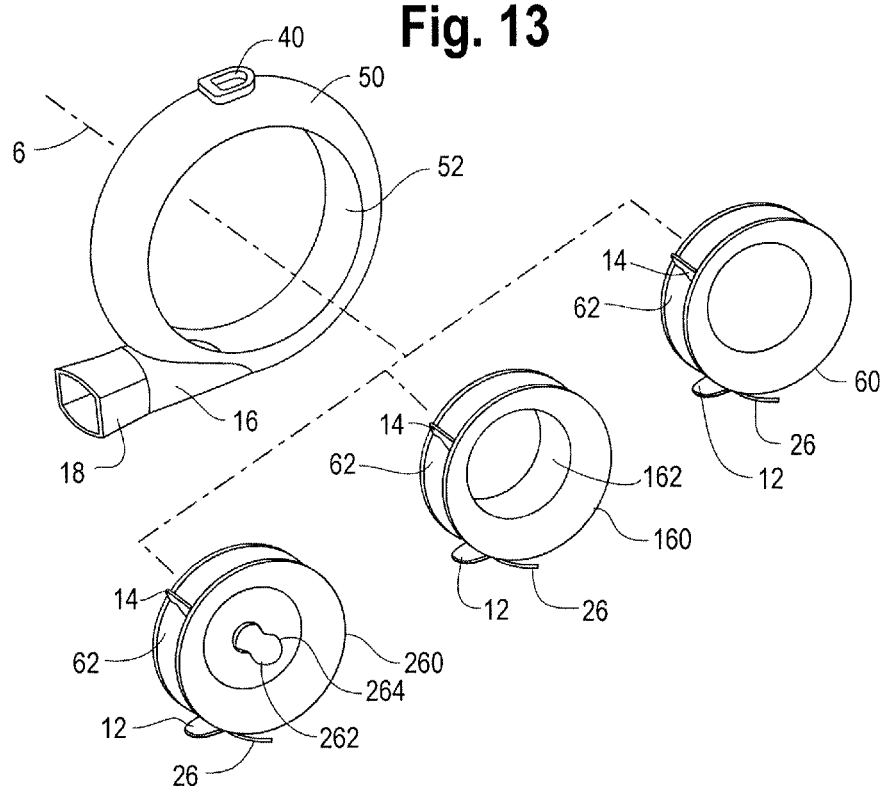

Referring to FIGS. 1-3 and 13-15, the inner ring-like housing component 60, 160, 260, 360, 460 may be configured in different ways. Indeed, in one embodiment a delivery device kit may be configured as a modular system, including for example an outer ring-like housing 40, and a plurality of differently configured inner ring-like housings 60, 160, 260, 360, 460. For example, as shown in FIGS. 1, 12 and 13, the inner ring-like housing component 60 may be symmetrical relative to the plane 10, with each side of the ring-like component having a curved shape in cross-section, whether concave or convex and with the central open space 8 configured as a through opening. In other embodiments, shown for example in FIGS. 2, 3, 14 and 15, the inner ring-like housing component 160, 260, 360, 460 is non-symmetrical. For example, as shown in the embodiment of FIG. 2, the inner ring-like housing component 460 includes a nasal mask 480 is positioned in the central opening 8 and in fluid communication with the delivery port. The mask 480 is positioned adjacent the inner periphery 30 so as to maintain the central space as a through opening to allow access by a user 94 to a soother device such as breast 90 or bottle 164.

As shown in FIG. 3, one side of the inner ring-like housing component 360 may be configured with an annular gasket 380 or mask extending substantially parallel to the axis from a "user" side of the housing. The mask may be configured with an irregular, non-circular shape, for example with a recess 380 shaped to fit over the outside of the user's nose. The gasket or wall seals with the user's face.

Figure 15:
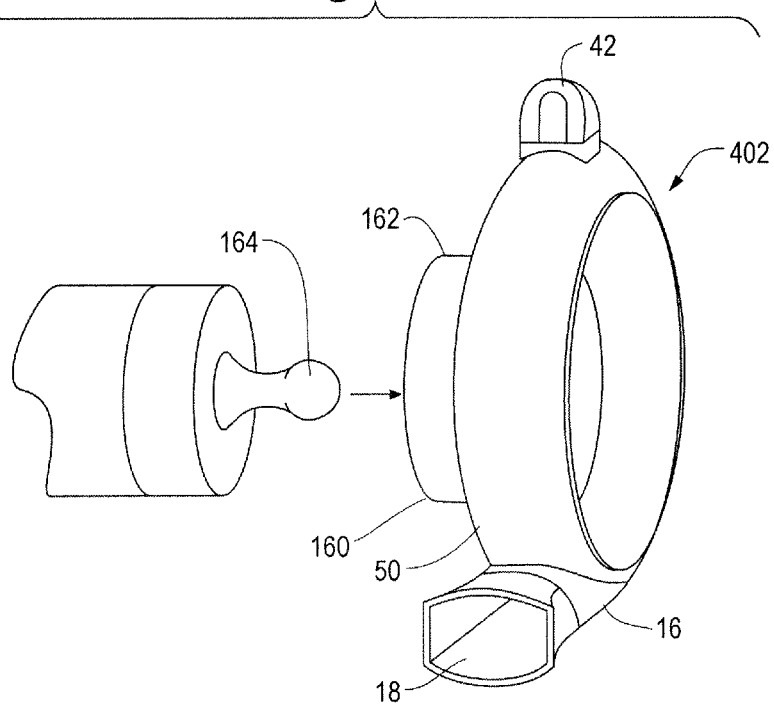
Figure 16:
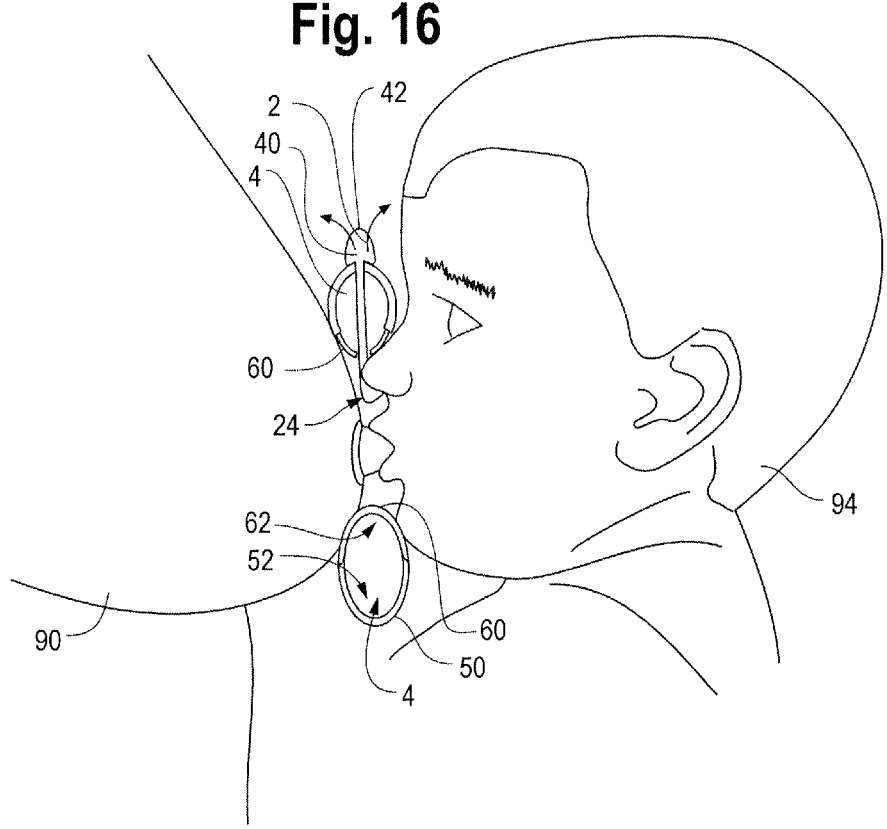

As shown in FIG. 15, the inner ring-like housing component 160 includes a gasket or wall 162 extending from an opposite provider side of the housing 4, but with the central space 8 being maintained as a through opening to allow access to a soother device such as a bottle 164. The gasket is shaped to engage and seal with a bottle filled for example with a fluid, such as milk or formula.

Figure 14:
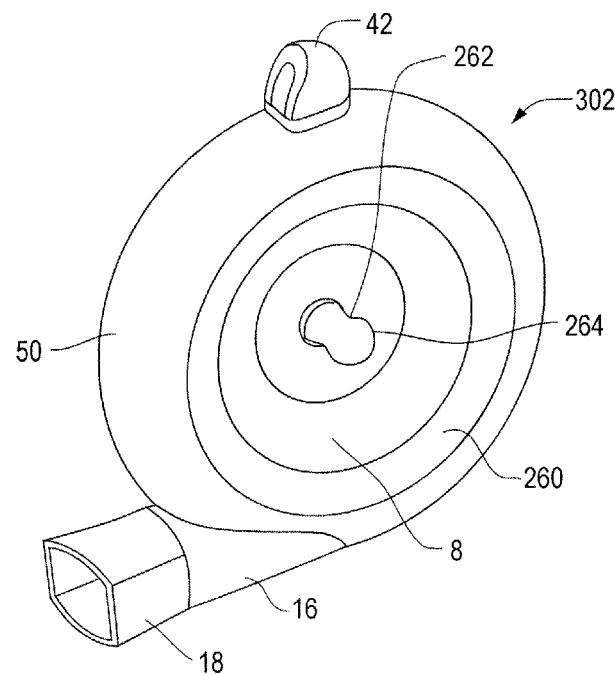

Referring to FIGS. 14 and 13, the central open space 8 is closed off on the provider side of the device with a wall 264, such that the central opening 8 is no longer a through opening. Rather, a soother device 262, configured as a nipple, extends from the wall 264 toward the user side where it may be accessed by the user 94.

It should be understood that in various embodiments, the various configurations of the inner ring-like housing 60, 160, 260, 360, 460 may be combined to provide a great number of different configurations suitable for various users, caregivers and situations. For example, the nasal mask 480 or the user gasket 380 may be combined with the wall 264 and soother device 262 or the bottle engaging gasket 162. One possible kit combination is shown in FIG. 3, wherein the caregiver is provided with three user soother interface options 60, 160, 260, including a breast feeding interface 60, a bottle interface 160 and a pacifier interface 260. Each of those interfaces, however, may be further configured with a nasal mask 480 or user gasket 380.

Referring to FIGS. 18-24, various alternative delivery devices are shown as including a holding chamber 700. The holding chamber may have various antistatic properties as disclosed above. As shown in FIGS. 18-21, the holding chamber has an input end 702 configured to mate with a delivery device 98, such as a pressurized metered dose inhaler. The holding chamber further includes an output end 704 configured with a baffle 712 and a one-way inhalation valve 714 in one embodiment. The output end may further include an annular flange 708 shaped to engage and support a user interface. The holding chamber may be configured with a visual indicator 706 that provides visual indicia when the user is exhaling and/or inhaling. Various suitable holding chambers are disclosed in U.S. Pat. Nos. 6,336,453, 7,360, 537, 6,904,908, the entire disclosures of which are hereby incorporated herein by reference.

As shown in FIGS. 18-21 and 25-27, the user interface is configured as a nasal mask 600, 707 having a flexible sealing edge 602, formed by a curved lip of the mask. The mask may be made of soft seal silicone, or other soft polymer. The sealing edge forms a generally triangular shaped opening 604, with curved sides. The opening has a curvilinear bottom edge 608, and curvilinear side edges 610 extending from the bottom edge and meeting at an apex 612. The user's nose fits in the opening 604, with the nostrils extending past the bottom edge into a cavity 614 formed in the mask. In other embodiments, the shape and size of the mask are configured to be positioned over the nose alone or the nose and mouth together. The apex 612 fits over the top of the patient's nose. In the embodiment shown in FIGS. 18-21, the mask 600 includes an annular mounting flange 616 shaped and configured to receive the end portion 708 of the holding chamber 700 or other substance delivery device. For example, a groove 617 may be formed around the inner periphery of the mounting flange 616, with the end portion 708 having an annular flange 719 extending radially outwardly and received in the groove.

Figure 24:
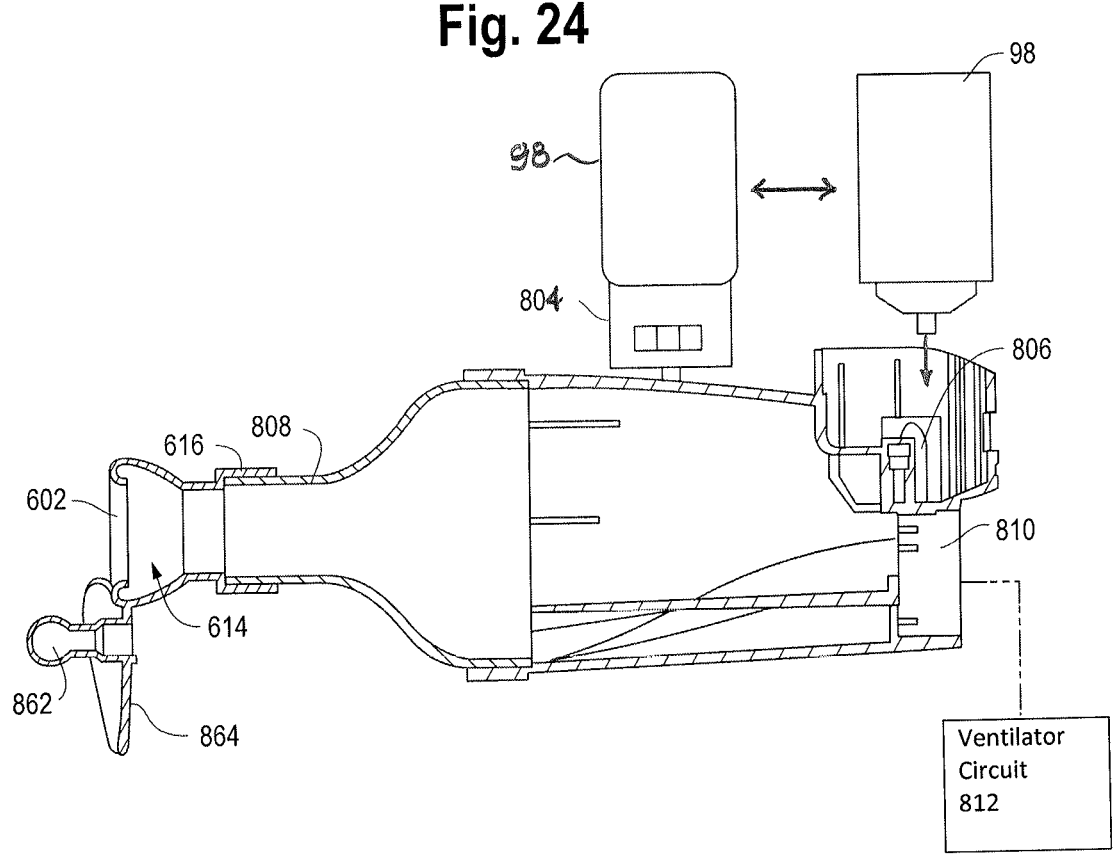
FIG. 24 is a cross-sectional view of the delivery device taken along line 24-24 of FIG. 23.
Figure 25:
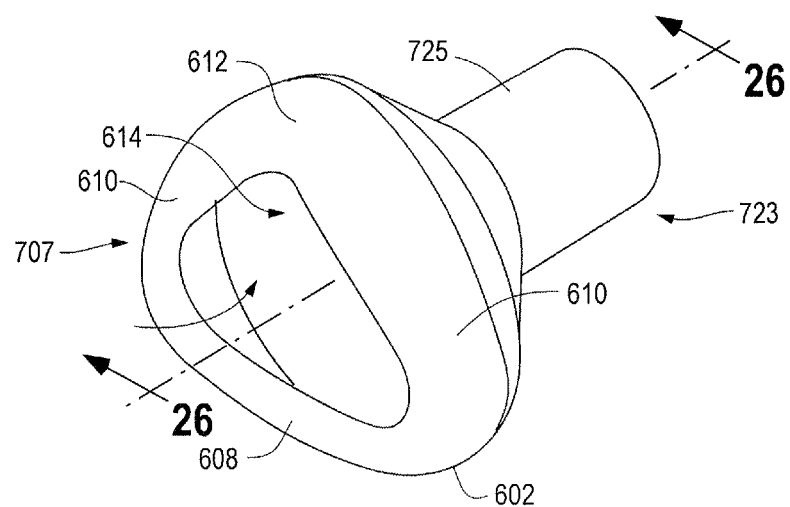
FIG. 25 is a perspective view of an alternative embodiment of a user interface.
Figure 27:
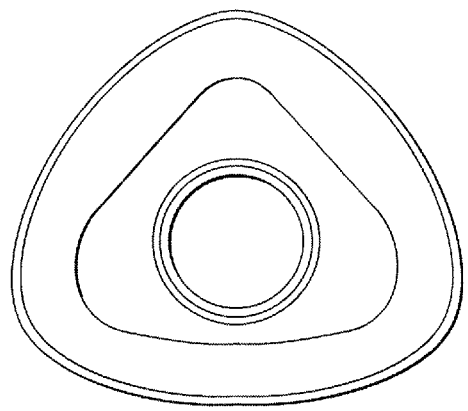
FIG. 27 is an end view of the user interface shown in FIG. 25.
Figure 26:
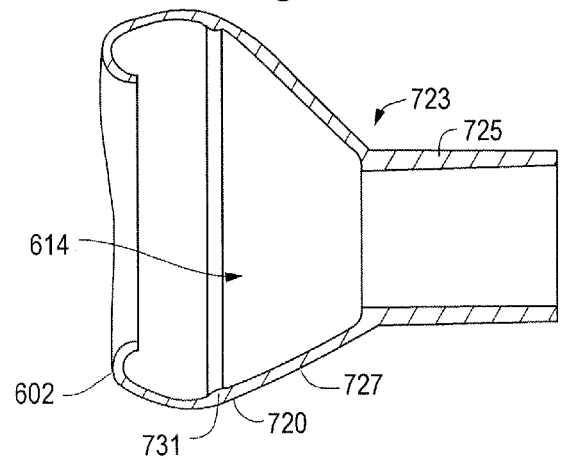
FIG. 26 is a cross-sectional view of the user interface shown in FIG. 25 taken along line 26-26.

As shown in FIGS. 25-27, the user interface is formed from two different materials. The mask 707 includes a sealing portion 602, or soft cushion seal as described above, that is coupled to a mounting portion 723. In particular, the mounting portion 723 includes an annular mounting flange 725, or tube, that may be received in or over an output end 704, 808 of a holding chamber 700, 800, configured in various embodiments as an annular flange 708, 808 or tube as shown for example in FIGS. 18, 19 and 22-24. The mounting portion 723 is made of a hard plastic, for example a plastic material that once molded maintains its shape and is not easily crushed, dented or deformed under application of a 16N load, while the sealing portion 707 is made of a softer polymer, such as a soft seal silicone, e.g., a liquid silicone rubber. Suitable examples of a hard plastic include without limitation nylon thermoplastics, such as nylon 6 or nylon 12, with the hard plastic being capable of withstanding, i.e., maintaining its shape, when exposed to the molding temperatures of the soft polymer, e.g., 300-350F for silicone. A soft polymer includes a plastic or rubber material that once molded maintains its shape, but with the shape being deformable, with the material providing only slight resistance under application of a 16N load, such that the soft polymer will form to the contours of the object against which it is pressed. In this embodiment, the mounting portion has a generally frusto-conically shaped interface portion 727 that extends longitudinally and radially outwardly from the mounting flange. The term "frusto-conical" refers to the frustum of a cone, with openings at both ends, but is further defined herein as including a linear or curved wall in cross-section. It should be understood that the interface portion may have other shapes. The interface portion 727 may define in part the cavity 614 shaped to receive the user's nose.

Figure 21:
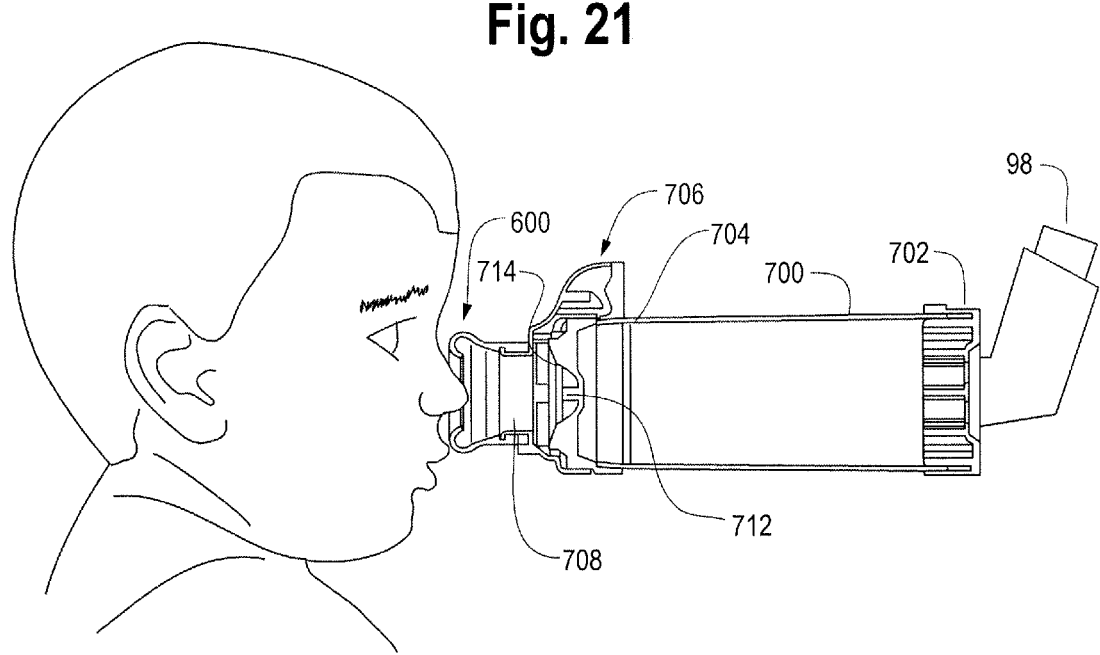

In one embodiment, the sealing portion 707 is overmolded and has an edge portion 729 overlying the edge 731 of the interface portion 727. The sealing portion 707 may be connected to the interface portion 727 with a chemical or mechanical overmolded bond. The mask 707 may be made in a two-shot molding process, wherein one or the other of the mounting portion 723 and sealing portion 707 is molded in a first shot, and then with the other of the mounting portion and sealing portion being overmolded on the first molded component in a second shot. For example, in one embodiment, the mounting portion 723 is molded in a first shot and the sealing portion 707 is overmolded onto the mounting portion in a second shot, the first and second shots may be carried out in separate molding machines, or by manipulating the piece with a tool and molding within the same machine. The mask 600 and sealing portion 707 define the cavity 614 that receives the user's nose, but with the mouth of the user accessible and open to the ambient environment below the sealing portion as shown in FIG. 21, allowing access for example of a soothing device. In other embodiments, the cavity receives the nose and mouth of the user.

Referring to FIGS. 41-48, various embodiments of the mask are particularly well suited for use with a nebulizer, such as AeroEclipse® II/L BAN nebulizer. When delivering medication using a nebulizer, the mask may need a pressure relief/exhalation valve 1002. In one embodiment, the pressure relief valve 1002 is integrated into the mask. As disclosed above, the mask is made with a two-shot design, including a mounting portion 1004 and a sealing portion 707. In particular, and referring to the embodiment of FIGS. 41-46, a hinged arm 1006, made of a rigid material such as nylon, is molded with the mounting portion 1004. A pressure relief valve 1002 is molded as part of the second shot with the sealing portion 707. The valve 1002 and arm 1006 are then moved and locked into a closed/locked position over an opening 1008 formed in the mounting portion. In this embodiment, the valve 1002, made for example of silicone, is molded in an open position together with the sealing portion. The valve may take any shape, including a polygonal shape such as a rectangle, or other shapes, including circular, oblong, oval, elliptical, triangular shapes etc. The hinged arm 1006 is then swung down to lock the valve 1002 in the closed/locked position, for example with a free end of the arm snapping into engagement with the mounting portion 1004. The arm 1006 overlies the valve 1002, with opposite sides of the valve 1002 being moveable away from the opening when a certain pressure is applied thereto from the interior of the mask. The pressure relief/exhalation valve 1002 provides minimal rebreathing of exhaled gases, while providing minimal leakage of air from the surrounding environment into the device during inhalation. The pressure relief valve 1002 avoids overpressurization of the user, e.g., neonate, when using the mask in combination with a nebulizer.

Alternatively, as shown in FIGS. 47 and 48, the valve 1002 is integrally molded as part of the second shot with the sealing portion 707. The valve 1002 is molded in a normally open position, spaced apart from the opening 1008. In operation, the valve 1002 closes in response to the inhalation pressure from the user. A bar 1009 is positioned across the opening and provides a portion of a valve seat, together with the perimeter of the opening 1008, with the bar 1009 acting to prevent the valve from moving into the interior of the mask. The valve 1002 moves to a normally open position during exhalation, or when no inhalation pressure is applied.

Figure 22:
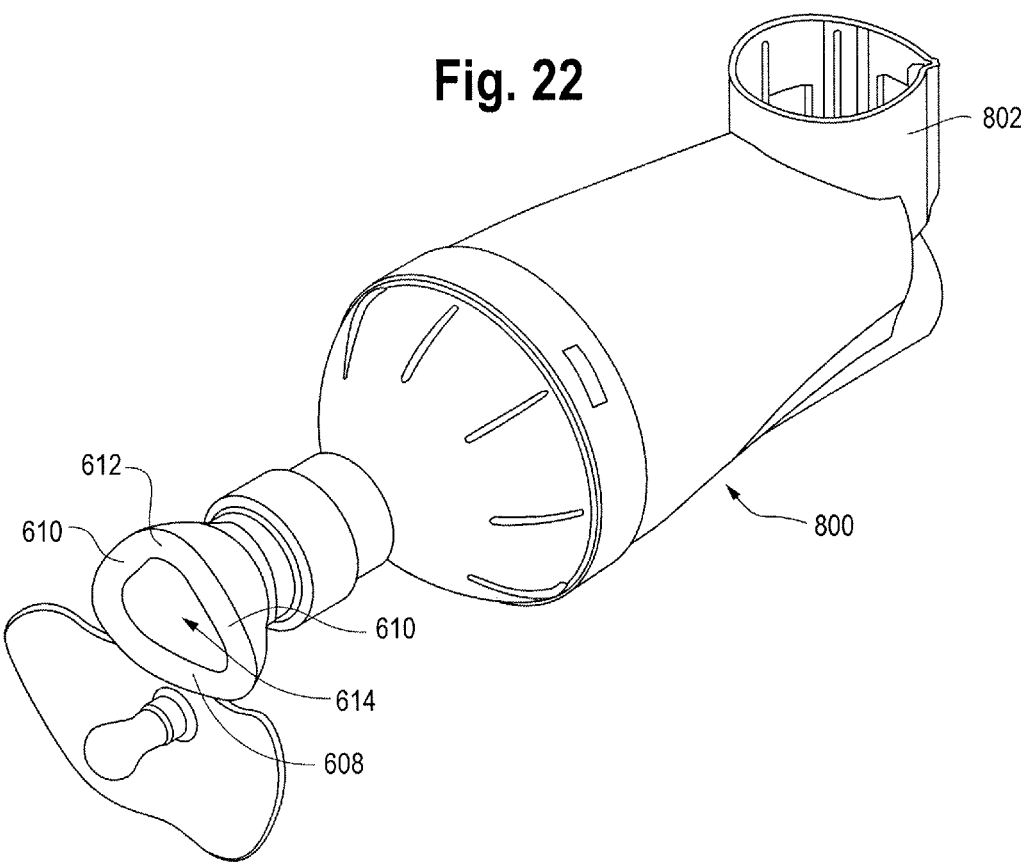
Figure 23:
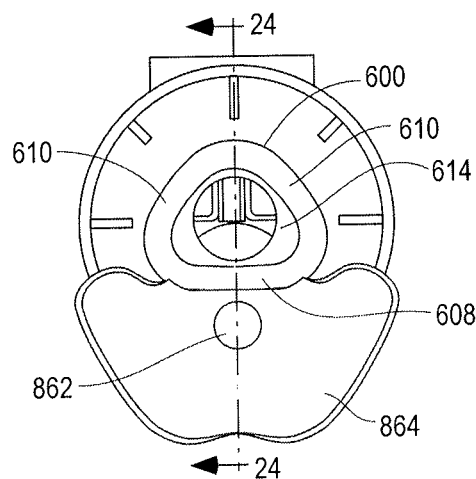
FIG. 23 is an end view of the delivery device shown in FIG. 22.

As shown in the embodiment of FIGS. 22-24, an alternative embodiment of a holding chamber 800 has a receptacle 802 for receiving the delivery device 98, which may be configured with a dose counter 804 in one embodiment. An actuator 806 actuates the dose counter when the delivery device is actuated. The holding chamber has an output end 808, which may further include an annular flange shaped to engage and support a user interface, such as the mask shown in FIGS. 18-21. The holding chamber may further include an input end 810 that is suitable for connection to a ventilator circuit 812 or other oxygen supply. Such holding chambers are further described and disclosed in U.S. Publication No. 2010/0101570 and U.S. Pat. No. 8,151,794, the entire disclosures of which are hereby incorporated herein by reference.

In this embodiment, the mask 600 further includes an integral soother device 862, or nipple, with a shield, or mouth guard 864, surrounding the soother device 362 and extends outwardly and downwardly therefrom. The shield or mouth guard has a contoured shaped suitable for mating with the chin and mouth of the user. The soother device 862 is connected to the bottom edge portion 608.

In operation, and referring to FIGS. 10-12 and 16, the housing 4 is positioned with a caregiver's breast 90 and nipple extending into the central open space 8 from a provider side of the housing. The inner ring-like housing component 60 seals against the breast 90 as shown in FIG. 12. The face of the user 94, including the nasal passageways 196 and the mouth 194, is then introduced to the central open space from the user side of the housing 4, with a mouth 194 of the user 94 latching onto the nipple of the breast 90, which functions as an oral soother device. The inner ring-like housing component 60, whether configured with a mask 480 or not, is sealed against the face of the user. If provided with a nasal mask 480, the device is positioned such that the nasal mask 480 overlies the nasal passageways 196 of the user. In alternative embodiments, other soother devices, such as a bottle nipple 164, or a pacifier nipple 262, are introduced to the user 94, who will latch onto such devices for oral soothing. When situated in these various configurations, the user may breath normally through their nose and nasal passageways 196, with air being inhaled from the input port 16 as the inhalation valve 26 opens, through the interior cavity or chamber 4 and through the delivery port 24 to the central open space 8. During exhalation, the air passes back through the delivery port 24 and through the exhalation port 40. During inhalation, the one-way exhalation valve 46 is closed, while during exhalation, the one-way inhalation valve 26 is closed, thereby creating a back-pressure and forcing the exhaled gases out through the exhalation port 40. The caregiver, whether the provider soothing the user, or a third party observer, may monitor the exhalation valve 46, and in particular the movement thereof, to confirm the patient is exhaling. Movement of the exhalation valve 46 also provides information about the quality of the seal between the breast 90 or bottle 164 and the inner ring-like housing component 60, 160 and between the user's face and the other side of the inner ring-like housing component. If the exhalation valve 46, or flow indicator, is not moving properly, the caregiver may reposition one of the breast 90, bottle 164 or user 94 to achieve better seals on both the provider and user sides of the housing 4.

Referring to the operation of the nasal mask of FIGS. 18-24, the mask 600 is placed over the nose of the infant, with the nostrils disposed in the cavity 614. The caregiver may monitor the visual flow indicator 706 to ensure a proper seal of the mask against the face of the infant. In the embodiment of FIGS. 22-24 and 25-27, the soother 862 may be placed in the mouth of the infant to provide comfort to the infant when the mask is placed over the nostrils.

Once a proper breathing cycle is achieved, a delivery device 98, secured to the input port 16, or receptacle, may be actuated to introduce an aerosolized medicament into the interior cavity through the input port 16. For example, the container 22 of a MDI may be reciprocally moved relative to an actuator boot 96 so as to release a metered dose of aerosolized medicament through a mouthpiece 20 coupled to the input port 16. The medicament is drawn from the interior chamber 4 through the delivery port 24 and into the central opening 8 or nasal mask 480, wherein the aerosolized medicament is inhaled by the user. The device may be actuated one or more times as needed and prescribed. The medicament or other inhalable substance, such as oxygen and/or an aromatic substance in vapor form, may be administered by a metered dose inhaler or nebulizer, and may be positioned in a ventilator circuit, or other system providing an oxygen supply 812.

Referring to FIGS. 28A-40, various delivery devices and kits, assembled and unassembled, are shown as including a mask 707, an adapter and a nebulizer 900. In each of the embodiments, a mask 707 as shown and described above with respect to FIGS. 25-27 may be used. The mounting portion 723, and in particular the annular flange 725, is connected to one or more embodiments of adapters.

For example, as shown FIGS. 28A-C, 37 and 38, an adapter 902 is configured as a T-connector, having a first end 904 with a port defined by an annular flange 906 that is dimensioned and shaped to receive the annular flange 725 of the mask. A second end 908 is configured with a second port 910 having a one-way relief, or exhalation, valve 912, which is positioned to allow exhaust gases to escape, but prevent ambient air from entering the adapter. A third port 914 extends from the adapter 90° relative to and axis of a conduit 916 defined between the first and second ends 904, 908. The third port 914 is in fluid communication with the substance dispenser, shown as a nebulizer 900.

Referring to FIGS. 29A-C, 39 and 40, an adapter 916 is configured with a T-connector 918 and a 90° elbow connector 920, each with inter-fitting annular flanges 922, 924. It should be understood that the T-connector and elbow connector may be integrally formed as a single component. The T-connector 918 includes a side port 926 having a one-way relief, or exhalation, valve 912. The T-connector defines a conduit 928 having a flow separator 930 disposed therein and defining an inhalation pathway 932 and an exhalation pathway 934 therethrough. The inhalation pathway 932 is in fluid communication with the nebulizer 900 via the elbow connector 920, while the exhalation pathway is in communication with side port 926 and relief valve 912.

Referring to FIGS. 30A-B, 32 and 33, an adapter 936 is configured with first, second and third T-connectors 938, 940, 942 arranged and fitted end-to-end to define a linear conduit 944, each with inter-fitting annular flanges 946, 948. It should be understood that the first, second and third T-connectors may be integrally formed as a single component. A nebulizer 900 is further coupled to the third T-connector 942. The first T-connector 938 includes a side port 950 having a one-way relief, or exhalation, valve 912. The first T-connector may or may not be configured with a flow separator. Second and third T-connectors 940, 942 include side ports 952, 954. A gravity chamber 956 has an input passageway 958 communicating with and connected to the side port 954 of the third T-connector 942 at a first location, and an output passageway 960 communicating with and connected to the side port 952 of the second T-connector 940 at a second location spaced from the first location. An elbow connector 962 may be disposed between the output passageway 960 of the gravity tank 956 and the side port 952 of the second T-connector to further define the output passageway.

Referring to FIGS. 31A-B, 35 and 36, an adapter 964 is configured with first and second T-connectors 964, 966 arranged and fitted end-to-end to define a linear conduit 968, each with inter-fitting annular flanges. It should be understood that the first and second T-connectors may be integrally formed as a single component. A nebulizer 900 is further coupled to the second T-connector 966. The first T-connector 964 includes a side port 970 having a one-way relief, or exhalation, valve 912. The first T-connector may or may not be configured with a flow separator. The second T-connector 966 includes a side port 972. A gravity chamber 974 includes a passageway 976 communicating with the side port 972. The second T-connector 966 includes a baffle 978 disposed in, and restricting flow through, the conduit 968 adjacent the side port opening. The baffle 978 may partially or completely obstruct the conduit 968, for example by forming a wall laying perpendicular to the axis of the conduit 968, forcing the flow path down into the passageway 976 of the gravity chamber as shown in FIG. 31A.

Referring to FIG. 34, an adapter is configured with T-connector 982 having a side port 986 with a one-way relief, or exhalation valve 912. A flexible tube 984 is connected to one end of the T-connector 982, for example by inter-fitting annular flanges, with the flexible tube and T-connector defining a conduit. The flexible tube 984, for example a flexible concertina tube having a plurality of bellows, may be manipulated to define a wide range of angles between axes of first and second ends thereof, as well as, and simultaneously, being extended or retracted to different lengths. The bellows of the flexible tube provide it with "memory," allowing the tube to be manipulated to a particular, predetermined angular position and/or length, and then released, with the tube maintaining the position without the tube returning to a previous or different position. A nebulizer 900 is further coupled to the flexible tube 984. The T-connector may or may not be configured with a flow separator.

Aerosolized medication that may be administered using the delivery devices, including the various adapter and nebulizers, including, without limitation, corticosteroids, such as beclamethasone, budesonide, flunisolide, ciclesonide, and fluticasone, and bronchodilators, such as albuterol, proventil, levalbuterol, salmeterol and pirbuterol.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A delivery device comprising:

a substance dispenser;

a mask in fluid communication with said substance dispenser, said mask comprising a mounting portion comprising a hard plastic coupled to a sealing portion comprising a soft polymer, said sealing portion comprising a bottom flexible edge portion, and a pair of flexible side portions, said side portions extending upwardly from said bottom portion and connecting at an apex, wherein said mounting portion comprises a hinged arm, said arm moveable from an open position to a closed position, and further comprising a valve, said, valve moveable from a first position to a second position as said arm is moved from said open position to said closed position, wherein said valve covers an opening in said mounting portion when moved to said second position.

2. The delivery device of claim 1 wherein said substance dispenser comprises an oxygen supply.

3. The delivery device of claim 1 wherein said substance dispenser dispenses an aromatic substance in vapor form.

4. The delivery device of claim 1 wherein said substance dispenser supplies a corticosteroid in aerosol form.

5. The delivery device of claim 1 wherein said substance dispenser supplies a bronchodilator in aerosol form.

6. The delivery device of claim 1 wherein said substance dispenser comprises a metered dose inhaler.

7. The delivery device of claim 1 wherein said substance dispenser comprises a nebulizer.

8. The delivery device of claim 1 wherein said mounting portion comprises a mounting tube and an interface portion connected to said mounting tube, wherein said sealing portion is coupled to said interface portion.

9. The delivery device of claim 8 wherein said interface portion has a generally frusto-conical shape.

10. The delivery device of claim 1 wherein said sealing portion is overmolded onto said mounting portion.

11. The delivery device of claim 1 further comprising an adapter disposed between said mask and said substance dispenser.

12. The delivery device of claim 11 wherein said adapter comprises a 90° elbow.

13. The delivery device of claim 11 wherein said adapter comprises a flexible tube.

14. The delivery device of claim 13 wherein said flexible tube comprises a concertina flexible tube.

15. The delivery device of claim 11 wherein said adapter further comprises a conduit, and a gravity chamber connected to said conduit.

16. The delivery device of claim 15 wherein said gravity chamber has an input passageway communicating with said conduit at a first location, and an output passageway communicating with said conduit at a second location spaced from said first location.

17. The delivery device of claim 15 wherein said gravity chamber comprises a passageway communicating with said conduit at an opening, and wherein said adapter further comprising a baffle disposed in, and restricting flow through, said conduit adjacent said opening.

18. A delivery device comprising:
a mask comprising a mounting portion comprising a hard plastic coupled to a sealing portion comprising a soft polymer; and
an adapter connected to said mounting portion of said mask, wherein said adapter comprises a first port connected to said mounting portion of said mask, a second port adapted to be connected to a substance dispenser, a third port spaced apart from said first and second port and an exhalation pathway defined between said first and third ports, wherein said third port comprises a one-way exhaust valve communicating between said exhalation pathway and an ambient environment.

19. The delivery device of claim 18 wherein said mounting portion comprises a mounting tube and an interface portion connected to said mounting tube, wherein said sealing portion is coupled to said interface portion, wherein said adapter is connected to said mounting tube.

20. The delivery device of claim 19 wherein said interface portion has a generally frusto-conical shape.

21. The delivery device of claim 18 wherein said sealing portion is overmolded onto said mounting portion.

22. The delivery device of claim 18 wherein said adapter comprises a 90° elbow.

23. The delivery device of claim 18 wherein said adapter comprises a flexible tube.

24. The delivery device of claim 18 wherein said adapter further comprises a conduit having a flow separator disposed therein and defining an inhalation pathway and said exhalation pathway.

25. The delivery device of claim 18 wherein said adapter further comprises a conduit, and a gravity chamber connected to said conduit.

26. The delivery device of claim 25 wherein said gravity chamber has an input passageway communicating with said conduit at a first location, and an output passageway communicating with said conduit at a second location spaced from said first location.

27. The delivery device of claim 25 wherein said gravity chamber comprises a passageway communicating with said conduit at an opening, and wherein said adapter further comprising a baffle disposed in, and restricting flow through, said conduit adjacent said opening.

28. The delivery device of claim 18 wherein an inhalation pathway is defined between said first and second ports, wherein said inhalation pathway is not obstructed by a valve.

* * * * *